United States Patent
Gemba et al.

(10) Patent No.: US 9,695,219 B2
(45) Date of Patent: *Jul. 4, 2017

(54) POLYPEPTIDE HAVING ANTIBACTERIAL ACTIVITY AND ANGIOGENESIS-INDUCING ACTIVITY AND WOUND-HEALING DRUG CONTAINING SAID POLYPEPTIDE

(71) Applicant: FUNPEP INC., Tokyo (JP)

(72) Inventors: Takefumi Gemba, Kawanishi-Hyogo (JP); Hideki Tomioka, Minoh (JP); Nao Tamura, Suita (JP); Ryoko Sata, Ibaraki (JP); Akito Maeda, Kyoto (JP); Akiko Tenma, Suita (JP); Toshihide Kanamori, Ikeda (JP); Yoshimi Saito, Toyonaka (JP); Shintaro Komaba, Ikeda (JP); Ryuichi Morishita, Suita (JP)

(73) Assignee: FunPep Inc., Tokyo (JP)

( * ) Notice: Subject to any disclaimer, the term of this patent is extended or adjusted under 35 U.S.C. 154(b) by 78 days.

This patent is subject to a terminal disclaimer.

(21) Appl. No.: 14/604,567

(22) Filed: Jan. 23, 2015

(65) Prior Publication Data

US 2015/0133365 A1 May 14, 2015

Related U.S. Application Data

(62) Division of application No. 13/322,424, filed as application No. PCT/JP2010/058838 on May 25, 2010, now Pat. No. 8,969,311.

(30) Foreign Application Priority Data

May 25, 2009 (JP) .................... 2009-125072

(51) Int. Cl.
| A61K 38/00 | (2006.01) |
| A61K 38/10 | (2006.01) |
| A61K 38/16 | (2006.01) |
| A61P 43/00 | (2006.01) |
| A61P 17/00 | (2006.01) |
| C07K 7/08 | (2006.01) |

(52) U.S. Cl.
CPC ............... *C07K 7/08* (2013.01); *A61K 38/10* (2013.01); *A61K 38/00* (2013.01)

(58) Field of Classification Search
None
See application file for complete search history.

(56) References Cited

U.S. PATENT DOCUMENTS

| 4,939,224 | A | 7/1990 | Musso et al. |
| 7,452,856 | B2 | 11/2008 | Nagaoka et al. |
| 7,674,771 | B2 | 3/2010 | Yoshida et al. |
| 7,807,176 | B2 | 10/2010 | Nishikawa et al. |
| 7,964,556 | B1 | 6/2011 | Kobayashi et al. |
| 8,012,749 | B2 | 9/2011 | Yano et al. |
| 8,470,765 | B2 | 6/2013 | Gemba et al. |
| 2005/0214321 | A1 | 9/2005 | Rasochova et al. |
| 2006/0122122 | A1 | 6/2006 | Kobayashi et al. |
| 2007/0032431 | A1 | 2/2007 | Yoshida et al. |
| 2007/0281888 | A1 | 12/2007 | Nishikawa et al. |
| 2008/0025962 | A1 | 1/2008 | Hayashi et al. |
| 2008/0069849 | A1 | 3/2008 | Schmidtchen et al. |
| 2009/0143319 | A1 | 6/2009 | Gemba et al. |
| 2009/0149632 | A1 | 6/2009 | Nagaoka et al. |
| 2010/0167390 | A1 | 7/2010 | Nakajima et al. |
| 2012/0052104 | A1 | 3/2012 | Gemba et al. |
| 2012/0122766 | A1 | 5/2012 | Gemba et al. |

FOREIGN PATENT DOCUMENTS

| EP | 2371840 A1 | 10/2011 |
| EP | 2404932 A1 | 1/2012 |
| JP | 2006-045214 A | 2/2006 |
| JP | 2006-160640 A | 6/2006 |
| JP | 2007-512842 A | 5/2007 |
| WO | WO 01/12668 A1 | 2/2001 |
| WO | WO 2005/049819 A1 | 6/2005 |
| WO | WO 2005/090564 A1 | 9/2005 |

(Continued)

OTHER PUBLICATIONS

Merriam-Webster, "Prevention", available online at www.merriam-webster.com/dictionary/prevention, 8 pages, (accessed on Jul. 10, 2016).*
Cambridge Academic Content Dictionary, "Disease", available online at http://dictionary.cambridge.org/us/dictionary/english/disease, 6 pages (accessed on Jul. 10, 2016).*
BiologyOnline, Disorder, available online at http://www.biology-online.org/dictionary/Disorder, 1 page (accessed on Jul. 10, 2016).*
Wound Care Centers, "Different Types of Wounds," available online at http://www.woundcarecenters.org/article/wound-basics/different-types-of-wounds, 6 pages, (accessed on Jul. 10, 2016).*
Berman et al., "Carbuncle," available online at https://medlineplus.gov/ency/article/000825.htm, 5 pages at p. 1, 1st and 3rd paragraphs (2015).*
Aurora et al., "Helix capping," *Protein Science*, 7(1): 21-38 (1998).
Brenneman et al., "Protective peptides that are orally active and mechanistically nonchiral," *J Pharmacol. Exp. Ther.*, 309(3): 1190-1197 (2004).

(Continued)

*Primary Examiner* — Hasan Ahmed
*Assistant Examiner* — Thea D'Ambrosio
(74) *Attorney, Agent, or Firm* — Leydig, Voit & Mayer, Ltd.

(57) ABSTRACT

A novel polypeptide which has an excellent angiogenesis-inducing activity and an excellent antibacterial activity, and a novel angiogenesis-inducing agent which contains the polypeptide as an effective ingredient or a novel agent for treating a wound(s) which contains the polypeptide as an effective ingredient are disclosed. The polypeptide of the present invention is a polypeptide whose amino acid sequence is shown in any one of SEQ ID NOs:1 to 6, 8 and 10. The angiogenesis-inducing agent which contains the polypeptide of the present invention as an effective ingredient is useful for the prevention, amelioration or treatment of a disease such as a burns, decubitus, wound, skin ulcer, leg ulcer, diabetic ulcer, occlusive arterial disease and arteriosclerosis obliteran.

15 Claims, 8 Drawing Sheets

(56) References Cited

FOREIGN PATENT DOCUMENTS

| WO | WO 2006/054947 A1 | 5/2006 |
|---|---|---|
| WO | WO 2008/096814 A1 | 8/2008 |
| WO | WO 2008/096816 A1 | 8/2008 |
| WO | WO 2010/061915 A1 | 6/2010 |
| WO | WO 2010/101237 A1 | 9/2010 |

OTHER PUBLICATIONS

Collado et al., "Vasoactive intestinal peptide enhances growth and angiogenesis of human experimental prostate cancer in a xenograft model," *Peptides*, 28: 1896-1901 (2007).
D'Andrea et al., "Targeting angiogenesis: structural characterization and biological properties of a de novo engineered VEGF mimicking peptide," *Proc. Natl. Acad. Sci. USA*, 102(40): 14215-14220 (2005).
Dharap et al., "Tumor-specific targeting of an anticancer drug delivery system by LHRH peptide," *Proc. Natl. Acad. Sci. USA*, 102(36): 12962-12967 (2005).
Hayward et al., "Fibroblast growth factor reserves the bacterial retardation of wound contraction," *Am. J. Surg.*, 163(3): 288-293 (1992).
Herouy et al., "Matrix metalloproteinases and venous leg ulceration," *Eur. J. Dermat.*, 10(3): 173-180 (2000).
Koczulla et al., "An angiogenic role for the human peptide antibiotic LL-37/hCAP-18," *J. Clin. Invest.*, 111(11): 1665-1672 (2003).
López-Garcia et al., "Anti-fungal activity of cathelicidins and their potential role in Candida albicans skin infection," *J. Invest. Dermatol.*, 125(1): 108-115 (2005).
Martinez et al., "Proadrenomedullin $NH_2$-terminal 20 peptide is a potent angiogenic factor, and its inhibition results in reduction of tumor growth," *Cancer Res.*, 64(18): 6489-6494 (2004).
Matsuzaki et al., "Control of cell selectivity of antimicrobial peptides," *Biochim. Biophys. Acta.*, 1788: 1687-1692 (2009).
Nakagami et al., "Anti-microbial Peptide and angiogenesis," *J. Jpn. Coll. Angiol.*, 48: 437-440 (2008).
Nakagami et al., "Modification of a novel angiogenic peptide, AG30, for the development of novel therapeutic agents," *J. Cell. Mol. Med.*, 16(7): 1629-1639 (2012).
Nishikawa et al., "Development of a novel antimicrobial peptide, AG-30, with angiogenic properties," *J. Cell. Mol. Med.*, 13(3): 535-546 (2009).
Nishikawa et al., "Analysis of de novo engineered variants of AG-30 for the treatment of ischemic diseases and infectious diseases," *J. Gene Med.*, 11(12): 1166-1167 (2009) [Abstract 37 for the 14th Annual Meeting of the Japan Society of Gene Therapy (Jun. 12-14, 2008)].
Sato et al., "Glycoinsulins: dendritic sialyloligosaccharide-displaying insulins showing a prolonged blood-sugar-lowering activity," *J. Am. Chem. Soc.*, 126(43): 14013-14022 (2004).
Sato et al., "Site-specific introduction of sialic acid into insulin," *Angew. Chem. Int. Ed.*, 43(12): 1516-1520 (2004).
Sawai et al., "Impact of single-residue mutations on the structure and function of ovispirin/novispirin antimicrobial peptides," *Protein Eng.*, 15(3): 225-232 (2002).
Shinoyama et al., "Cutaneous Ulceration," *Japanese Journal of Clinical Dialysis*, 24(7): 819-821 (2008).
Stenberg et al., "Effect of bFGF on the inhibition of contraction caused by bacteria," *J. Surg. Res.*, 50(1): 47-50 (1991).
Strömstedt et al., "Evaluation of strategies for improving proteolytic resistance of antimicrobial peptides by using variants of EFK17, an internal segment of LL-37," *Antimicrobial Agents and Chemotherapy*, 53: 593-602 (2009).
Ulbricht et al., "The use of PEG-Hirudin in chronic hemodialysis monitored by the Ecarin Clotting Time: influence on clotting of the extracorporeal system and hemostatic parameters," *Clin. Nephrol.*, 65(3): 180-190 (2006).
Uniprot, UNIProtKB/TreEMBL Protein Accession No. COPK96 [http://www.uniprot.org/unitprot/C0PK96] (Jul. 2012).
Wilkemeyer et al., "Ethanol antagonist peptides: structural specificity without stereospecificity," *J. Pharmacol. Exp. Ther.*, 309(3): 1183-1189 (2004).
Zanetti et al., "Cathelicidins, multifunctional peptides of the innate immunity," *J. Leukoc. Biol.*, 75(1): 39-48 (2004).
Zasloff, "Magainins, a class of antimicrobial peptides from Xenopus skin: isolation, characterization of two active forms, and partial cDNA sequence of a precursor," *Proc. Natl. Acad. Sci. USA*, 84(15): 5449-5453 (1987).
European Patent Office, European Search Report in European Patent Application No. 10780549 (Dec. 18, 2012).
European Patent Office, Extended European Search Report in European Patent Application No. 09829160.2 (Jun. 17, 2012).
Japanese Patent Office, International Search Report in International Patent Application No. PCT/JP2009/070035 (Dec. 28, 2009).
Japanese Patent Office, International Preliminary Report on Patentability in International Patent Application No. PCT/JP2009/070035 (Jul. 5, 2011).
Japanese Patent Office, Written Opinion of the International Searching Authority for PCT/JP2009070035 filed (Jul. 5, 2011).
Japanese Patent Office, International Search Report in International Patent Application No. PCT/JP2010/053618 (May 25, 2010).
Japanese Patent Office, International Preliminary Report on Patentability in International Patent Application No. PCT/JP2010/053618 (Oct. 18, 2011).
Japanese Patent Office, Written Opinion of the International Searching Authority in International Patent Application No. PCT/JP2010/053618 (May 25, 2010).
Japanese Patent Office, International Search Report in International Patent Application No. PCT/JP2010/058838 (Sep. 14, 2010).
Japanese Patent Office, International Preliminary Report on Patentability in International Patent Application No. PCT/JP2010/058838 (Dec. 12, 2011).
Japanese Patent Office, Written Opinion of the International Searching Authority in International Patent Application No. PCT/JP2010/058838 (Sep. 14, 2010).
United States Patent and Trademark Office, Office Action in U.S. Appl. No. 13/131,796 (Dec. 12, 2013).
United States Patent and Trademark Office, Response to Office Action of Dec. 12, 2013 in U.S. Appl. No. 13/131,796 (Mar. 13, 2014).
United States Patent and Trademark Office, Office Action in U.S. Appl. No. 13/131,796 (May 7, 2014).
United States Patent and Trademark Office, Interview Summary in U.S. Appl. No. 13/131,796 (Jun. 16, 2014).
United States Patent and Trademark Office, Response to Office Action of May 7, 2014, filed with RCE in U.S. Appl. No. 13/131,796 (Sep. 8, 2014).
United States Patent and Trademark Office, Terminal Disclaimer filed in U.S. Appl. No. 13/131,796 and relating to the term of U.S. Appl. No. 13/322,424 (Sep. 25, 2014).

* cited by examiner

\* p<0.01(t-test)

\* p<0.01(t-test)

* p<0.05(t-test: Compared with control group)

Wound Healing (%)

* p<0.05(t-test: Compared with control group)

```
                              SEQUENCE LISTING

<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: SR-1, chemically synthesized peptide

<400> SEQUENCE: 1

Met Leu Lys Leu Ile Phe Leu His Arg Leu Lys Arg Met Arg Lys Arg
1               5                   10                  15

Leu Lys Arg Lys
            20

<210> SEQ ID NO 2
<211> LENGTH: 21
<212> TYPE: PRT
<213> ORGANISM: Artificial Sequence
<220> FEATURE:
<223> OTHER INFORMATION: SR-2, chemically synthesized peptide
<220> FEATURE:
<221> NAME/KEY: MISC_FEATURE
<222> LOCATION: (21)..(21)
<223> OTHER INFORMATION: Xaa is Arg-amidated

<400> SEQUENCE: 2

Glu Leu Arg Phe Leu His Arg Leu Lys Arg Arg Leu Arg Lys Arg Leu
1               5                   10                  15

Lys Arg Lys Leu Xaa
            20

<210> SEQ ID NO 3
<211> LENGTH: 20
<212> TYPE: PRT
<213> ORGANISM: Artificial Sequence
<220> FEATURE:
<223> OTHER INFORMATION: SR-3, chemically synthesized peptide
<220> FEATURE:
<221> NAME/KEY: MISC_FEATURE
<222> LOCATION: (20)..(20)
<223> OTHER INFORMATION: Xaa is Arg-amidated

<400> SEQUENCE: 3

Glu Leu Arg Phe Leu His Arg Leu Lys Arg Met Arg Lys Arg Leu Lys
1               5                   10                  15

Arg Lys Leu Xaa
            20

<210> SEQ ID NO 4
<211> LENGTH: 20
<212> TYPE: PRT
<213> ORGANISM: Artificial Sequence
<220> FEATURE:
<223> OTHER INFORMATION: SR-4, chemically synthesized peptide
<220> FEATURE:
<221> NAME/KEY: MISC_FEATURE
<222> LOCATION: (20)..(20)
<223> OTHER INFORMATION: Xaa is Arg-amidated

<400> SEQUENCE: 4

Lys Leu Ile Phe Leu His Arg Leu Lys Arg Met Arg Lys Arg Leu Lys
1               5                   10                  15
```

Arg Lys Leu Xaa
            20

<210> SEQ ID NO 5
<211> LENGTH: 20
<212> TYPE: PRT
<213> ORGANISM: Artificial Sequence
<220> FEATURE:
<223> OTHER INFORMATION: SR-5, chemically synthesized peptide

<400> SEQUENCE: 5

Lys Arg Met Arg Lys Arg Leu Lys Arg Lys Leu Arg Leu Trp His Arg
1               5                   10                  15

Lys Arg Tyr Lys
            20

<210> SEQ ID NO 6
<211> LENGTH: 18
<212> TYPE: PRT
<213> ORGANISM: Artificial Sequence
<220> FEATURE:
<223> OTHER INFORMATION: SR-6, chemically synthesized peptide
<220> FEATURE:
<221> NAME/KEY: MISC_FEATURE
<222> LOCATION: (18)..(18)
<223> OTHER INFORMATION: Xaa is Lys-amidated

<400> SEQUENCE: 6

Met Arg Lys Arg Leu Lys Arg Lys Leu Arg Leu Trp His Lys Arg
1               5                   10                  15

Tyr Xaa

<210> SEQ ID NO 7
<211> LENGTH: 30
<212> TYPE: PRT
<213> ORGANISM: Artificial Sequence
<220> FEATURE:
<223> OTHER INFORMATION: AG30-5C, chemically synthesized peptide

<400> SEQUENCE: 7

Met Leu Lys Leu Ile Phe Leu His Arg Leu Lys Arg Met Arg Lys Arg
1               5                   10                  15

Leu Lys Arg Lys Leu Arg Phe Trp His Arg Lys Arg Tyr Lys
            20                  25                  30

<210> SEQ ID NO 8
<211> LENGTH: 19
<212> TYPE: PRT
<213> ORGANISM: Artificial Sequence
<220> FEATURE:
<223> OTHER INFORMATION: SR-08, 17 Lys is D-amino acid, chemically
      synthesized peptide
<220> FEATURE:
<221> NAME/KEY: MISC_FEATURE
<222> LOCATION: (17)..(17)
<223> OTHER INFORMATION: Xaa is D-Lys
<220> FEATURE:
<221> NAME/KEY: MISC_FEATURE
<222> LOCATION: (19)..(19)
<223> OTHER INFORMATION: Xaa is Lys-amidated

<400> SEQUENCE: 8

Leu Lys Leu Ile Phe Leu His Arg Leu Lys Arg Met Arg Lys Arg Leu
1               5                   10                  15

Xaa Arg Xaa

```
<210> SEQ ID NO 9
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: PAMP
<220> FEATURE:
<221> NAME/KEY: misc_feature
<222> LOCATION: (20)..(20)
<223> OTHER INFORMATION: Xaa is Arg-amidated

<400> SEQUENCE: 9

Ala Arg Leu Asp Val Ala Ser Glu Phe Arg Lys Lys Trp Asn Lys Trp
1               5                   10                  15

Ala Leu Ser Xaa
            20

<210> SEQ ID NO 10
<211> LENGTH: 20
<212> TYPE: PRT
<213> ORGANISM: Artificial Sequence
<220> FEATURE:
<223> OTHER INFORMATION: SR-07, 18 Lys is D-amino acid, chemically
      synthesized peptide
<220> FEATURE:
<221> NAME/KEY: MISC_FEATURE
<222> LOCATION: (18)..(18)
<223> OTHER INFORMATION: Xaa is D-Lys

<400> SEQUENCE: 10

Met Leu Lys Leu Ile Phe Leu His Arg Leu Lys Arg Met Arg Lys Arg
1               5                   10                  15

Leu Xaa Arg Lys
            20

<210> SEQ ID NO 11
<211> LENGTH: 18
<212> TYPE: PRT
<213> ORGANISM: Artificial Sequence
<220> FEATURE:
<223> OTHER INFORMATION: AP00196, chemically synthesized peptide

<400> SEQUENCE: 11

Lys Asn Leu Arg Arg Ile Ile Arg Lys Ile Ile His Ile Ile Lys Lys
1               5                   10                  15

Tyr Gly
```

POLYPEPTIDE HAVING ANTIBACTERIAL ACTIVITY AND ANGIOGENESIS-INDUCING ACTIVITY AND WOUND-HEALING DRUG CONTAINING SAID POLYPEPTIDE

CROSS-REFERENCE TO RELATED APPLICATIONS

The present application is a division of U.S. patent application Ser. No. 13/322,424, which was filed on Nov. 23, 2011, and which issued as U.S. Pat. No. 8,969,311 on Mar. 3, 2015, which is the US national phase of International Patent Application PCT/JP2010/058838, filed on May 25, 2010. This previous application is hereby incorporated by reference herein. Priority is claimed to Japanese Patent Application 2009-125072, filed on May 25, 2009. This application is also incorporated by reference herein.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: one 4,544 Byte ASCII (Text) file named "722603SequenceListing$_{13}$ ST25.txt," created Feb. 15, 2017.

TECHNICAL FIELD

The present invention relates to novel polypeptides which have an angiogenesis-inducing activity and an antibacterial activity, as well as an angiogenesis-inducing agent containing the polypeptide and an agent for treating a wound(s) containing the polypeptide.

BACKGROUND ART

In the treatment of various diseases or injuries including burns, decubituses, wounds, skin ulcers, leg ulcers, diabetic ulcers, occlusive arterial disease and arteriosclerosis obliterans, angiogenesis is useful. Since serious exacerbation of the pathological condition may be induced by bacterial infection in these diseases, an angiogenesis-inducing agent or an agent for treating a wound(s), which has both an antibacterial activity and an angiogenesis-inducing activity, is demanded.

As a polypeptide which has an angiogenesis-inducing activity and an antibacterial activity, LL-37 is known (Non-Patent Literatures 1 and 2).

Besides, Nakagami et al. invented a polypeptide which has a vascular endothelial growth activity, and in turn, an angiogenesis-inducing activity, and further discovered that the peptide has a higher angiogenesis-inducing activity than LL-37, and then filed a patent application directed thereto (Patent Literature 1). Furthermore, Nakagami et al. discovered a polypeptide AG30-5C, which consists of 30 amino acid residues and has a higher angiogenesis-inducing activity than the peptide of Patent Literature 1, and then filed a patent application directed thereto (Patent Literature 2).

Patent Literatures 1 and 2 also disclose that the polypeptides have an antibacterial activity.

In addition, as a peptide which exhibits an angiogenesis-inducing activity with a low dosage, Proadrenomedullin NH$_2$-Terminal 20 peptide (PAMP) is known (Non-patent Literature 3).

PRIOR ART REFERENCES

Patent Literatures

Patent Literature 1 WO 2005/090564 A1
Patent Literature 2 WO 2008/096816 A1

Non-Patent Literatures

Non-patent Literature 1: Koczulla R, von Degenfeld G, Kupatt C, Krotz F, Zahler S, Gloe T, Issbrucker K, Unterberger P, Zaiou M, Lebherz C, Karl A, Raake P, Pfosser A, Boekstegers P, Welsch U, Hiemstra P S, Vogelmeier C, Gallo R L, Clauss M, Bals R., "An angiogenic role for the human peptide antibiotic LL-37/hCAP-18.", J Clin Invest. 2003 June; 111(11):1665-72

Non-patent Literature 2: Zanetti M., "Cathelicidins, multifunctional peptides of the innate immunity.," J Leukoc Biol. 2004 January; 75(1):39-48. Epub 2003 Jul. 22.

Non-patent Literature 3: Martinez A, Zudaire E, Portal-Nunez S, Guedez L, Libutti S K, Stetler-Stevenson W G, Cuttitta F. "Proadrenomedullin NH$_2$-terminal 20 peptide is a potent angiogenic factor, and its inhibition results in reduction of tumor growth." Cancer Res. 2004 Sep. 15; 64(18): 6489-94.

SUMMARY OF THE INVENTION

Problems to be Solved by the Invention

An object of the present invention is to provide a novel polypeptide which has a higher angiogenesis-inducing activity and a higher antibacterial activity and a novel angiogenesis-inducing agent which contains the polypeptide as an effective ingredient or a novel agent for treating a wound(s) which contains the polypeptide as an effective ingredient.

Means for Solving the Problems

The present inventors discovered polypeptides which have a higher vascular endothelial growth activity, and in turn, a higher angiogenesis-inducing activity, than previous polypeptides. In addition, these polypeptides had a higher antibacterial activity than conventional polypeptides.

The present inventors intensively studied to discover, by searching analogs of the polypeptides as described in Patent Literatures 1 and 2, polypeptides which have a higher angiogenesis-inducing activity and a higher antibacterial activity than the polypeptides, thereby completing the present invention.

That is, the present invention relates to:
(1) A polypeptide whose amino acid sequence is shown in any one of SEQ ID NOs:1 to 6, 8 and 10.
(2) The polypeptide according to (1), whose amino acid sequence is shown in any one of SEQ ID NOs:1 to 6 and 8.
(3) The polypeptide according to (1), whose amino acid sequence is shown in SEQ ID NO:10.
(4) The polypeptide according to any one of (1) to (3), whose carboxyl terminus is amidated.
(5) An angiogenesis-inducing agent comprising the polypeptide according to any one of (1) to (4) as an effective ingredient.
(6) An antibacterial agent comprising the polypeptide according to any one of (1) to (4) as an effective ingredient.

(7) A method for inducing angiogenesis, said method comprising administering an effective amount of the polypeptide according to any one of (1) to (4) to a mammal in need of angiogenesis.
(8) A polypeptide for inducing angiogenesis, which is the polypeptide according to any one of (1) to (4).
(9) An agent for the prevention, amelioration or treatment of a disease(s) or disorder(s) selected from the group consisting of burns, wounds, erosions, skin ulcers and intractable wounds, said agent comprising the polypeptide according to any one of (1) to (4) as an effective ingredient.
(10) The agent for the prevention, amelioration or treatment according to (9), wherein the disease(s) or disorder(s) selected from the group consisting of burns, wounds, erosions, skin ulcers and intractable wounds is(are) associated with bacterial or fungal infection.
(11) The agent for the prevention, amelioration or treatment according to (9), wherein the disease(s) or disorder(s) is(are) selected from the group consisting of burns, wounds, erosions, skin ulcers and intractable wounds.
(12) A method for the prevention, amelioration or treatment of a disease(s) or disorder(s) selected from the group consisting of burns, wounds, erosions, skin ulcers and intractable wounds, said method comprising topically administering an effective amount of the polypeptide according to any one of (1) to (4).
(13) The method for the treatment according to (12), wherein the disease(s) or disorder(s) selected from the group consisting of burns, wounds, erosions, skin ulcers and intractable wounds is(are) associated with bacterial or fungal infection.
(14) The method for the treatment according to (12), wherein infection of the disease(s) or disorder(s) selected from the group consisting of burns, wounds, erosions, skin ulcers and intractable wounds is prevented.
(15) A polypeptide for use in the prevention, amelioration or treatment of a disease(s) or disorder(s) selected from the group consisting of burns, wounds, erosions, skin ulcers and intractable wounds, which is the polypeptide according to any one of (1) to (4).

Effects of the Invention

By the present invention, a polypeptide which has an excellent angiogenesis-inducing activity and an excellent antibacterial activity was provided. A novel angiogenesis-inducing agent which contains the polypeptide as an effective ingredient was also provided.

MODE FOR CARRYING OUT THE INVENTION

Figure 1:
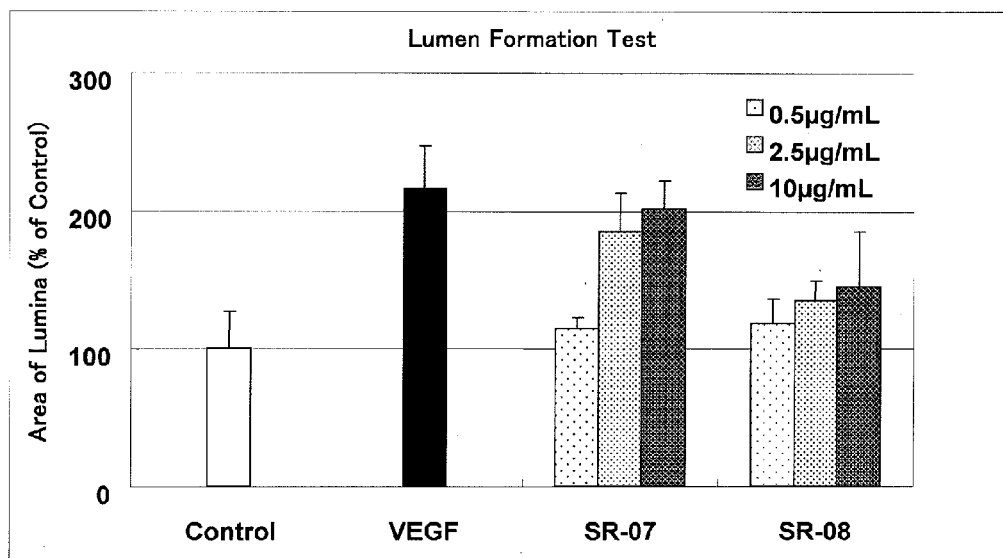
FIG. 1 shows the results of lumen formation test performed on the polypeptides SR-07 and SR-08 which are the examples of the present invention.

As described above, the polypeptide of the present invention is a polypeptide whose amino acid sequence is shown in any one of SEQ ID NOs:1 to 6, 8, 10 and 11. In the present description, the terms "polypeptide" and "peptide" are used synonymously.
The amino acid sequence of AG30-5C, which is the polypeptide described in Patent Literature 2, is shown in SEQ ID NO:7. As concretely described in Patent Literature 2 and the Examples below, AG30-5C has an antibacterial activity and an angiogenesis-inducing activity. Various analogs of AG30-5C were produced, and the angiogenesis-inducing activity and antibacterial activity of them were examined. As a result, it was proved that the above-described polypeptides of the present invention have an angiogenesis-inducing activity and an antibacterial activity. As concretely described in the Examples below, the polypeptides which are the examples of the present invention had a higher angiogenesis-inducing activity and a higher antibacterial activity than AG30-5C.
All of the polypeptides, each of which is the effective ingredient of the angiogenesis-inducing agent of the present invention, are novel substances.

In general, with respect to a pharmaceutical composed of a polypeptide(s), techniques to increase the stability of the polypeptide(s) in vivo, wherein a sugar chain(s) and/or a polyethylene glycol (PEG) chain(s) is(are) added to the polypeptide(s), or wherein a D-amino acid(s) is(are) used as at least one part of the amino acids constituting the polypeptide(s), are widely known and used. The addition of a sugar chain(s) and/or a PEG chain(s) to a polypeptide, or the use of a D-amino acid(s) as at least one part of the amino acids constituting a polypeptide makes the polypeptide more unlikely to be decomposed by a peptidase(s) in vivo, and in turn, makes the half-life of the polypeptide in vivo longer. It is also well known that acetylation of the N-terminus and/or amidation of the C-terminus of a peptide increases the stability of the peptide. The polypeptides of the present invention may be polypeptides which are modified with these known modifications for the stabilization in vivo, as long as they have an antibacterial activity. And, the term "polypeptide" as used herein and in the appended claims includes polypeptides which are modified with a modification(s) for the stabilization in vivo, unless the context clearly dictates otherwise.

The addition of a sugar chain to a polypeptide is well known, and described, for example, in Sato M, Furuike T, Sadamoto R, Fujitani N, Nakahara T, Niikura K, Monde K, Kondo H, Nishimura S., "Glycoinsulins: dendritic sialyloligosaccharide-displaying insulins showing a prolonged blood-sugar-lowering activity.", J Am Chem Soc. 2004 Nov. 3; 126(43):14013-22, and Sato M, Sadamoto R, Niikura K, Monde K, Kondo H, Nishimura S, "Site-specific introduction of sialic acid into insulin.", Angew Chem Int Ed Engl. 2004 Mar. 12; 43(12):1516-20. A sugar chain can be bound to N-terminus, C-terminus or the amino acid therebetween, but it is preferred that a sugar chain be bound to N-terminus or C-terminus, in order not to inhibit the activity of the polypeptide. And, the number of the sugar chains to be added is preferably one or two, more preferably one. The sugar chain is preferably from mono- to tetra-saccharide, more preferably disaccharide or trisaccharide. The sugar chain(s) can be bound directly to a free amino group(s) or a carboxyl group(s) on the polypeptide, or through a spacer structure(s) such as a methylene chain whose number of carbon atoms is about 1 to 10.

The addition of a PEG chain to a polypeptide is also well known, and described, for example, in Ulbricht K, Bucha E, Poschel K A, Stein G, Wolf G, Nowak G., "The use of PEG-Hirudin in chronic hemodialysis monitored by the Ecarin Clotting Time: influence on clotting of the extracorporeal system and hemostatic parameters.", Clin Nephrol. 2006 March; 65(3):180-90, and Dharap S S, Wang Y, Chandna P, Khandare J J, Qiu B, Gunaseelan S, Sinko P J, Stein S, Farmanfarmaian A, Minko T., "Tumor-specific targeting of an anticancer drug delivery system by LHRH peptide.", Proc Natl Acad Sci USA. 2005 Sep. 6; 102(36): 12962-7. A PEG chain can be bound to N-terminus, C-terminus or the amino acid therebetween, and one or two PEG chains are usually bound to a free amino group(s) and/or carboxyl group(s) on the polypeptide. The molecular weight of the PEG chain is not particularly limited, but typically about 3000 to 7000, preferably about 5000.

The method for changing at least one part of the amino acids constituting the polypeptide into D-isomer is also well known, and described, for example, in Brenneman D E, Spong C Y, Hauser J M, Abebe D, Pinhasov A, Golian T, Gozes I., "Protective peptides that are orally active and mechanistically nonchiral.", J Pharmacol Exp Ther. 2004 June; 309(3):1190-7, and Wilkemeyer M F, Chen S Y, Menkari C E, Sulik K K, Charness M E., "Ethanol antagonist peptides: structural specificity without stereospecificity.", J Pharmacol Exp Ther. 2004 June; 309(3):1183-9. One part of the amino acids constituting the polypeptide may be a D-amino acid(s), but it is preferred that all of the amino acids constituting the polypeptide be D-amino acids, in order to inhibit the activity of the polypeptide as little as possible.

Examples of the pharmaceutically acceptable salts of the present invention include, for example, a salt with an inorganic acid such as hydrochloric acid, sulfuric acid, nitric acid and phosphoric acid; and a salt with an organic acid such as acetic acid, trifluoroacetic acid, lactic acid, tartaric acid, oxalic acid, maleic acid, methanesulfonic acid, benzenesulfonic acid and p-toluenesulfonic acid. Among these, hydrochloric acid salt, acetic acid salt, or trifluoroacetic acid salt is more preferable.

In addition, the polypeptides of the present invention are not limited to the above-described polypeptides, as long as they have substantially the same effects. Therefore, for example, polypeptides consisting of the amino acid sequences whose one or more amino acids are substituted, deleted and/or added are also included.

The polypeptides which are the effective ingredients of the angiogenesis-inducing agents of the present invention can be easily produced by conventional methods such as a chemical synthesis method using a commercially available peptide synthesizer. In addition, the above-described modifications for the stabilization can be also easily carried out by well-known methods as described in each of the above-mentioned documents.

Since the polypeptides of the present invention have a high angiogenesis-inducing activity, they can be used as an angiogenesis-inducing agent. The methods of using them as angiogenesis-inducing agents are the same as known polypeptide-based angiogenesis-inducing agents. They can be administered as solutions, emulsions, suspensions, dusts, powders, granules, gels, ointments, or transdermal patchs, especially preferably as solutions, dusts, or transdermal patchs. Preferably, a buffer solution, especially preferably a solution dissolved in an aqueous medium such as a physiological saline buffer solution, can be administered as the solution. The concentration of the polypeptide in the solution is not particularly limited, but usually about 0.001 mg/mL to 100 mg/mL, preferably about 0.001 mg/mL to 10 mg/mL, about 0.1 mg/mL to 5 mg/mL, especially preferably about 1 mg/mL to 10 mg/mL. In general, the administration route is a topical administration such as applying and injecting to a site(s) which require(s) angiogenesis. The dosage may be appropriately selected depending on the symptom, the size of the affected part, or the like. In general, the dosage is, in terms of the polypeptide, about 0.001 mg to 100 mg, preferably about 0.005 mg to 50 mg, especially preferably about 0.01 mg to 10 mg, but not limited to these ranges, of course. As a pharmaceutically acceptable carrier which is used in formulating the angiogenesis-inducing agent of the present invention, in addition to the aqueous medium as mentioned above, carriers which are commonly used in the field of pharmaceutical formulation can be used. For example, in the case of an external preparation such as an ointment, the pharmaceutically acceptable carriers include hydrocarbons (hydrophilic petrolatum, white petrolatum, purified lanolin, liquid paraffin, etc.), zinc oxide, higher fatty acids and the esters thereof (adipic acid, myristic acid, palmitic acid, stearic acid, oleic acid, adipic acid ester, myristic acid ester, palmitic acid ester, diethyl sebacate, hexyl laurate, cetyl isooctanoate, etc.), waxes (spermaceti, beeswax, ceresin, etc.), and higher alcohols (cetanol, stearyl alcohol, cetostearyl alcohol, etc.). In the case of a solution, the pharmaceutically acceptable carriers include water, physiological saline, and phosphate-buffered physiological saline, for example. In the case of an oral preparation, the pharmaceutically acceptable carriers include lactose and starch, for example. In addition to these, as necessary, various pharmaceutical additives such as emulsifiers, surfactants, isotonic agents, pH adjustors can also be added. These pharmaceutically acceptable carriers and pharmaceutical additives are well known in the field of pharmaceutical formulation and used widely.

Specific examples of diseases and disorders in cases where the polypeptide of the present invention and the agent for the prevention, amelioration and treatment which contains the polypeptide as an effective ingredient are administered to a living body include, but not limited to, burns, wounds (including cut wounds and surgical wounds, and, in the present description, this provision being also applied hereinafter), erosions and skin ulcers (including decubituses (bedsores), burn ulcers, traumatic ulcers, leg ulcers (including varicose syndrome), postherpetic ulcers, radiation ulcers, drug ulcers, diabetic ulcers and postoperative ulcers, and, in the present description, this provision being also applied hereinafter); and burns, wounds and skin ulcers associated with infection; and intractable wounds (including those associated with infection and/or ulcers). The term "skin ulcer" refers to the condition wherein the damage (defect or necrosis) reaches dermis (see, for example, the Japanese Journal of Clinical Dialysis, vol. 24, No. 7, 2008, 819-921), in other words, refers to the condition wherein the epidermal layer is fully defective or necrotic and the dermal layer is also, fully or partially, defective or necrotic (see, for example, Eur. J. Dermat. Vol. 10, No. 3, 2000, 173-80). In general, wounds associated with skin ulcers are also referred to as intractable wounds or intractable skin ulcers. Since wounds associated with ulcers are more serious wounds and the polypeptides of the present invention show a therapeutic effect also in skin ulcers, those skilled in the art would be able to understand that these will exhibit a therapeutic effect also against wounds that are less serious than ulcers (including burns).

In the present description, the term "treatment" includes not only completely disappearing the above-described wounds and ulcers, but also partially reducing the area of the wounds and ulcers. Further, in the present description, the terms "treatment" and "amelioration" include promoting the complete disappearance and partial reduction of the area of the wounds and ulcers.

The polypeptide of the present invention and the agent for the prevention, amelioration and treatment which contains the polypeptide as an effective ingredient can be used as an agent for the prevention, amelioration or treatment for these diseases or disorders. Since the polypeptide of the present invention and the agent for the prevention, amelioration and treatment which contains the polypeptide as an effective ingredient have not only a high angiogenesis-inducing activity but also an antibacterial activity, they are especially suited as an agent for the prevention, amelioration or treatment of diseases or disorders which is desired to have an antibacterial activity as well. Examples of such diseases or disorders include, among the above-mentioned diseases or disorders, burns, decubituses, wounds and skin ulcers. In addition, the polypeptide of the present invention and the agent for the prevention, amelioration and treatment which contains the polypeptide as an effective ingredient are also useful not only for burns, wounds, erosions and skin ulcers which are associated with infection, but also for preventing infection to the above diseases or disorders which are not associated with infection.

The polypeptides of the present invention exhibit an antibacterial activity against bacteria (including aerobic bacteria and anaerobic bacteria) and fungi, and have broad antibacterial spectra. Therefore, the polypeptides of the present invention are useful not only for burns, wounds, erosions and skin ulcers which are infected with these broad range of bacteria (including secondary infection); and burns, wounds and skin ulcers associated with infection; and intractable wounds (including those associated with infection and/or ulcers) and other traumas, but also for preventing infection to these broad range of bacteria. For example, the polypeptides of the present invention are useful for the treatment, amelioration and prevention of skin infection of *Escherichia coli, Pseudomonas aeruginosa, Staphylococcus aureus, Klebsiella pneumoniae*, enterobacteria or the like. For example, the polypeptide of the present invention and the agent for the prevention, amelioration and treatment which contains the polypeptide as an effective ingredient can be used not only for promoting the healing of a surgical wound after suturing in a surgical operation (promoting granulation is included), but also for preventing infection thereof (including secondary infection). Of course, they can be also used for healing the infection of infected surgical wounds and/or the wounds per se.

In addition, since the polypeptides of the present invention have an angiogenesis activity, they can be also used as an agent for treating occlusive arterial disease and arteriosclerosis obliterans.

The polypeptide of the present invention and the agent for the prevention, amelioration and treatment which contains the polypeptide as an effective ingredient can be used individually, and, if further antimicrobial properties are desired, they can be used in combination with other antibacterial agents or antibiotics. Examples of such antibacterial agents or antibiotics include cephem, carbapenem, aminoglycoside, new quinolone, β-lactam, penicillin and glycopeptide antibiotics and the like, and more particularly include ceftazidime, meropenem, tobramycin, ciprofloxacin, methicillin, ampicillin, vancomycin and the like, but not limited thereto.

EXAMPLES

The present invention will now be described more concretely by way of Examples. However, the present invention is not limited to the Examples below.

Example 1

1. Synthesis of the Polypeptides

Protected peptide resins were synthesized by Fmoc method using a full-automatic solid-phase synthesizer according to the method described in documents such as Solid Phase Peptide Synthesis, Pierce (1984), Fmoc solid synthesis: a practical approach, Oxford University Press (2000) and The Fifth Series of Experimental Chemistry, Vol. 16, Synthesis of Organic Compounds IV. To the obtained protected peptide resins, trifluoroacetic acid (TFA) and a scavenger (a mixture of thioanisole, ethanedithiol, phenol, triisopropylsilane, water, etc.) were added to obtain crude peptides by cleaving from the resins and deprotecting. These crude peptides were purified by gradient elution using a reversed-phase HPLC column (ODS) in 0.1% TFA-H$_2$O/CH$_3$CN system. Fractions containing the desired substances were collected and freeze-dried to obtain the desired peptides. The amino acid sequences of the synthesized peptides were confirmed by using an amino acid sequencer G1000A (Hewlett Packard), PPSQ-23A (SHIMADZU CORPORATION) or ProciscLC (ABI).

The sequences of the peptides are shown below. With respect to SR-2, SR-3, SR-4 and SR-6, their C-termini are amidated, and these amidated peptides were used in the below-described Examples. In the sequence listing, with respect to these peptides whose C-termini are amidated, only their amino acid sequences are shown.

```
SR-1
                                           (SEQ ID NO: 1)
MLKLIFLHRLKRMRKRLKRK

SR-2
                                           (SEQ ID NO:2)
ELRFLHRLKRRLRKRLKRKLR-amide SR-3
                                           (SEQ ID NO: 3)
ELRFLHRLKRMRKRLKRKLR-amide SR-4
                                           (SEQ ID NO: 4)
KLIFLHRLKRMRKRLKRKLR-amide SR-5
                                           (SEQ ID NO: 5)
KRMRKRLKRKLRLWHRKRYK SR-6
                                           (SEQ ID NO: 6)
MRKRLKRKLRLWHRKRYK-amide AG30-5C
                                           (SEQ ID NO: 7)
MLKLIFLHRLKRMRKRLKRKLRFWHRKRYK SR-08
                                           (SEQ ID NO: 8)
LKLIFLHRLKRMRKRLK*RK-amide
(K*: D-Lys)

PAMP
                                           (SEQ ID NO: 9)
ARLDVASEFRKKWNKWALSR-amide
```

2. Analysis of the Polypeptides Using MALDI-TOF/MS

The sequences of the synthesized polypeptides were confirmed by the results of analysis using MALDI-TOF/MS. To 1 µL of a solution containing the polypeptide in 0.1% TFA/50% acetonitrile, whose final concentration was 100 µg/mL, 1 µL of a matrix solution (α-Cyano 4-Hydroxy Cinnamic Acid) was added to obtain a measurement sample for MALDI. The measurement sample for MALDI (0.4 µL) was applied on a MALDI target plate and dried, followed by measurement using MALDI-TOF/MS.

MALDI-TOF/MS Conditions:

Laser intensity: 2100

Number of shots: 1000

Results

The theoretical value and measured value of MALDI-TOF/MS for each polypeptide were shown in Table 1. The detected m/z of each polypeptide was matched to each theoretical value, and the sequences of the synthesized polypeptides were confirmed.

TABLE 1

| Polypeptide | MH+ (Da) | |
|---|---|---|
| | Theoretical value | Measured value |
| SR-1 | 2664.711405 | 2664.7424 |
| SR-2 | 2870.897365 | 2870.9932 |
| SR-3 | 2732.752685 | 2732.7961 |
| SR-4 | 2688.788005 | 2688.7334 |
| SR-5 | 2836.790145 | 2837.0413 |
| SR-6 | 2551.610055 | 2551.5486 |
| AG30-5C | 4135.558675 | 4135.9741 |

TABLE 2

| Polypeptide | MH+ (Da) | |
|---|---|---|
| | Theoretical value | Measured value |
| SR-08 | 2532.686895 | 2532.7292 |
| PAMP | 2460.373995 | 2460.5696 |

3. Angiogenesis-Inducing Activity of the Polypeptides

Using AG30-5C as a positive control, the angiogenesis-inducing activity of SR-1 and SR-2 was measured. More concretely, using an angiogenesis kit (Angiogenesis Kit, KZ-1000, KURABO INDUSTRIES LTD.), the ability of the polypeptides to form lumina was evaluated. As a negative control, polypeptide-free group (Control) was used.

Each polypeptide was added to a special medium for angiogenesis (KURABO INDUSTRIES LTD., KZ-1500) such that the concentration thereof was 10 µg/mL. Cells were cultured at 37° C. under 5% $CO_2$ in a 24-well plate using the special media to which the polypeptide was added. The medium was replaced with a medium containing the same polypeptide on Day 4, Day 7 and Day 9 of culture. On Day 11 from the beginning of the culture, the medium was removed and staining was performed using a kit for staining lumina (for CD31 antibody staining) according to the following procedure.

The primary antibody (mouse anti-human CD31 antibody) was 4000-fold diluted with a blocking solution (Dulbecco's phosphate buffered saline (PBS(−)) containing 1% BSA). To each well, 0.5 mL of this primary antibody solution was added, and the plate was incubated for 60 minutes at 37° C. After the completion of the incubation, each well was washed totally 3 times with 1 mL of the blocking solution.

Then, 0.5 mL of a secondary antibody solution (goat anti-mouse IgG/alkaline phosphatase conjugate) 500-fold diluted with the blocking solution was added to each well. The plate was incubated for 60 minutes at 37° C., and thereafter each well was washed 3 times with 1 mL of distilled water. During that period, 2 tablets of BCIP/NBT were dissolved into distilled water, and the obtained solution was filtered through a filter having a pore size of 0.2 µm to prepare a substrate solution. To each well, 0.5 mL of the prepared BCIP/NBT substrate solution was added, and the plate was incubated at 37° C. until the lumina turned to deep purple (typically for 5-10 minutes). After the completion of the incubation, each well was washed 3 times with 1 mL of distilled water. After washing, the washing solution was removed by aspiration, and the plate was left to stand and dry naturally. After drying, photographs of each well were taken under a microscope.

Each of the obtained images was quantified using an angiogenesis quantification software. Computer analysis was carried out on various parameters. And, on the basis of its scale, the lengths of formed lumina observed in each visual field were measured, and the effect of adding the polypeptides compared with Control was evaluated.

The results are shown in Tables 3 and 4.

TABLE 3

| Polypeptide | The Length of Lumina (Percentage when taking Control as 100) |
|---|---|
| SR-1 | 124.3 |
| SR-2 | 124.6 |
| AG30-5C | 119.1 |

As shown in Table 3, both SR-1 and SR-2, which are the polypeptides of the present invention, individually had an angiogenesis-inducing activity. Their activity was higher than AG30-5C.

TABLE 4

| Polypeptide | The Length of Lumina (Percentage when taking Control as 100) |
|---|---|
| SR-08 | 174.3 |
| PAMP | 124.6 |
| AG30-5C | 165.7 |

Furthermore, as shown in Table 4, SR-08, which is the polypeptide of the present invention, had an angiogenesis-inducing activity. Its activity was higher than AG30-5C and PAMP.

4. Antibacterial Activity of the Polypeptides

The antibacterial activity of the polypeptides was measured using an ATP assay method.

Using BacTiter-Glo Microbial Cell Viability Assay kit available from PROMEGA, the antibacterial activity of the peptides was evaluated from the viability of bacteria. In other words, ATP amount in viable bacteria in cases where the concentration of the peptides was 10 μg/mL was measured using a microtiter plate or test tubes.

With respect to the strains, *Staphylococcus aureus* ATCC29213 (*S. aureus* ATCC29213) as Gram-positive bacteria, or, alternatively, *Pseudomonas aeruginosa* (*P. aeruginosa* ATCC27853) as Gram-negative bacteria, was used. The bacteria were cultured in media for 3 to 4 hours, and thereafter absorbances at $A_{600}$ were measured. Bacterial suspensions were diluted with Mueller-Hinton broth (MHB) according to McFarland #0.5. Each strain was added so as to attain about $0.5-1\times10^5$ CFU/mL (final concentration) in terms of *Escherichia coli*. Each peptide was prepared and added to a microplate or test tubes so as to attain a final concentration of 10 μg/mL, and the bacterial suspension was added thereto. A solution to which the peptides were not added was considered as a negative control, and a solution to which tobramycin (TOB) was added was considered as a positive control. The plate was incubated at 37° C. for 3 hours, and the amount of ATP in the culture media was measured. Relative values were calculated by comparison with the negative control, and these values were regarded as the viability.

The results are shown in Table 5.

TABLE 5

| | Viability (%) | |
|---|---|---|
| Compound | *Staphylococcus aureus* | *Pseudomonas aeruginosa* |
| TOB | 3.5 | 1.8 |
| SR-1 | 21.9 | 31.0 |
| SR-2 | 8.0 | 4.2 |
| SR-3 | 11.2 | 9.3 |
| SR-4 | 2.1 | 13.2 |
| SR-6 | 16.2 | 20.2 |
| AG30-5C | 29.1 | 12.9 |

As shown in Table 3, SR-1, SR-2, SR-3, SR-4 and SR-6, which are the polypeptides of the present invention, individually had a higher antibacterial activity against *Staphylococcus aureus* than AG30-5C. Also, SR-2 and SR-3 individually had a higher antibacterial activity against *Pseudomonas aeruginosa* than AG30-5C.

Example 2

1. Synthesis of the Polypeptides

The polypeptide of the present invention, SR-07, and a control polypeptide, AP00196, were synthesized in the same manner as in Example 1, and the amino acid sequences of the synthesized polypeptides were each confirmed in the same manner as in Example 1. The sequences of these polypeptides were as follows.

```
SR-07
                              (SEQ ID NO: 10)
MLKLIFLHRLKRMRKRLK*RK

AP00196 (Control)
                              (SEQ ID NO: 11)
KNLRRIIRKIIHIIKKYG
```

2. Antibacterial Activity of the Polypeptides (ATP Assay)

The antibacterial activity of each of SR-08 and SR-07 polypeptides was measured using an ATP assay method. That is, using BacTiter-Glo Microbial Cell Viability Assay kit available from PROMEGA, the antibacterial activity of the peptides was evaluated from the viability of bacteria. In other words, ATP amount in viable bacteria in cases where the concentration of the peptides was 10 μg/mL was measured using a microtiter plate or test tubes. As controls, tobramycin (TOB), oxacillin (OX) and meropenem (MEPM) were used at the concentrations as respectively shown in Table 6 below.

TABLE 6

| | Concentration of Positive Controls (μg/mL) | | | | | |
|---|---|---|---|---|---|---|
| | *Escherichia coli* | *Pseudomonas aeruginosa* | *Staphylococcus aureus* | *Klebsiella pneumoniae* | Enterobacteria (1) | Enterobacteria (2) |
| TOB | 1.0 | 1.0 | 1.0 | 4.0 | 4.0 | 4.0 |
| OX | 1.0 | 1.0 | 0.125 | 4.0 | 4.0 | 4.0 |
| MEPM | 0.5 | 0.5 | 0.5 | 0.5 | 0.5 | 0.5 |

With respect to the strains, *Escherichia coli:* ATCC 25922 (*Escherichia coli* ATCC 25922), *Pseudomonas aeruginosa:* ATCC 27853 (*Pseudomonas aeruginosa* ATCC 27853), *Staphylococcus aureus:* ATCC29213 (*Staphylococcus aureus* ATCC29213), *Klebsiella pneumoniae:* JCM 1662 (*Klebsiella pneumoniae* JCM 1662), enterobacteria (1): JCM 1232 (*Enterobacter cloacae* JCM 1232), and enterobacteria (2): JCM 1235 (*Enterobacter aerogenes* JCM 1235), were used.

The bacteria were cultured in media for 3 to 4 hours, and thereafter absorbances at $A_{600}$ were measured. Bacterial suspensions were diluted with Mueller-Hinton broth (MHB) according to McFarland #0.5. Each strain was added so as to attain about $0.5$-$1 \times 10^5$ CFU/mL (final concentration) in terms of *Escherichia coli*. Each peptide was prepared and added to a microplate or test tubes so as to attain a final concentration of 10 µg/mL, and the bacterial suspension was added thereto. The plate was incubated at 37° C. for 3 hours, and the amount of ATP in the culture media was measured. Relative values were calculated by comparison with the negative control, and these values were regarded as the viability.

The results (mean values) are shown in Table 7 below.

efficacy of an antibacterial agent, for the strength of bacterial sensitivity, or the like. The bacteria can grow (proliferate) when the concentration is not higher than MIC, and cannot grow when the concentration is higher than MIC. Its measurement is carried out according to a method defined as a standard method by Japanese Society of Chemotherapy or CLINICAL AND LABORATORY STANDARD INSTITUTE (CLSI), but, in this Example, its measurement was carried out by a broth microdilution method in accordance with "M100-S17/M7-A7" (Performance Standards for Antimicrobial Susceptibility Testing; Seventeenth Informational Supplement, Vol. 27 No. 1) published by CLSI on January, 2007. That is, sensitivity test of agents was carried out using a microtiter plate or test tubes.

The bacteria were cultured in liquid media for 4 to 6 hours, and thereafter absorbances at $A_{600}$ were measured. Bacterial suspensions were diluted with Mueller-Hinton broth (MHB) according to McFarland #0.5. Each strain was added so as to attain about $10^5$ CFU/ml (final concentration). Each peptide was prepared to an optional concentration, and the solutions were serially diluted from the concentration. The polypeptide at each concentration stage was added to a microplate or test tubes, and the bacterial suspension was

TABLE 7

|  | *Escherichia coli* | *Pseudomonas aeruginosa* | *Staphylococcus aureus* | *Klebsiella pneumoniae* | Enterobacteria (1) | Enterobacteria (2) |
| --- | --- | --- | --- | --- | --- | --- |
| TOB | 4.1 | 1.5 | 3.4 | 4.6 | 2.9 | 0.7 |
| OX | 91.6 | 96.7 | 73.3 | 134.9 | 107.6 | 108.4 |
| MEPM | 12.4 | 19.3 | 89.8 | 9.2 | 3.8 | 1.7 |
| AP 00196 | 0.8 | 27.3 | 1.9 | 5.1 | 2.4 | 0.8 |
| SR-07 | 7.1 | 8.1 | 1.0 | 11.9 | 3.3 | 16.5 |
| SR-08 | 3.9 | 2.1 | 1.1 | 7.9 | 3.5 | 13.8 |

As shown in Table 7, the polypeptides of the present invention had broad antibacterial spectra.

3. Antibacterial Activity of the Polypeptides (MIC Measurement)

Further, with respect to not only the above-described strains but also various other strains, the "minimum inhibitory concentration (MIC)" was measured as follows. MIC is the lowest concentration of an agent that may inhibit the growth of a bacterium. MIC is used as a parameter for the added thereto. Chloramphenicol, amphotericin B, ciprofloxacin, meropenem (MEPM), ciprofloxacin (CPFX), tobramycin (TOB) and oxacillin (OX) were used as positive controls. The plate was incubated at 37° C. for 20 hours, and the lowest concentration where bacterial growth was inhibited was regarded as the minimum inhibitory concentration.

The results (MIC) of various bacteria are shown in Tables 8-1 to 8-3 below.

TABLE 8-1

|  | Bacterial Name | SR-07 | SR-08 | AP 00196 | Chloramphenicol | Amphotericin B | Tobramycin | Meropenem | Oxacillin | Ciprofloxacin |
| --- | --- | --- | --- | --- | --- | --- | --- | --- | --- | --- |
| Aerobic bacteria | *Escherichia coli* | 64/128 | 32/64 | 8/16 |  |  | 0.25-1.0 | 0.008-0.06 | — | N.T. |
|  | *Micrococcus luteus* | 2 | 1 | 2 | 1 | N.T. | N.T. | N.T. | N.T. | N.T. |
|  | *Bacillus subtilis* | 2 | 2 | 2 | 4 | N.T. | N.T. | N.T. | N.T. | N.T. |
|  | *Salmonella enteritidis* | 8 | 4 | 16 | 4 | N.T. | N.T. | N.T. | N.T. | N.T. |
|  | *Salmonella typhimurium* | 8 | 8/4 | 16 | 4 | N.T. | N.T. | N.T. | N.T. | N.T. |
|  | *Streptococcus pyogenes* | 64 | 64 | 32 | 2 | N.T. | N.T. | N.T. | N.T. | N.T. |
|  | *Pseudomonas aeruginosa* | 16/32 | 32 | 16/32 | N.T. | N.T. | 0.25-1.0 | 0.25-1.0 | — | N.T. |
|  | *Pseudomonas aeruginosa* (clinical strain 1) | 16/64 | 16 | 16/64 | N.T. | N.T. | ≥16 | <4 | — | <1 |
|  | *Pseudomonas aeruginosa* (clinical strain 6) | 16/64 | 16/32 | 32/64 | N.T. | N.T. | <4 | 8 | — | <1 |
|  | *Pseudomonas aeruginosa* (clinical strain 8) | 32/128 | 16/32 | 32/64 | N.T. | N.T. | <4 | <4 | — | <1 |
|  | *Pseudomonas aeruginosa* (clinical strain 9) | 32/128 | 16/64 | 32/128 | N.T. | N.T. | <4 | <4 | — | <1 |

TABLE 8-1-continued

| Bacterial Name | SR-07 | SR-08 | AP 00196 | Chloramphenicol | Amphotericin B | Tobramycin | Meropenem | Oxacillin | Ciprofloxacin |
|---|---|---|---|---|---|---|---|---|---|
| *Pseudomonas aeruginosa* (clinical strain 12) | 16/32 | 16/32 | 16/32 | N.T. | N.T. | <4 | <4 | — | >4 |
| *Staphylococcus epidermidis* | 8/16 | 8≥ | 8/16 | N.T. | N.T. | 0.12-1.0 | 0.03-0.12 | 0.15-0.5 | N.T. |
| *Staphylococcus aureus* | 16/32 | 16 | 16 | N.T. | N.T. | 0.12-1.0 | 0.03-0.12 | 0.15-0.5 | N.T. |
| MSSA (clinical strain 1) | 32 | 16/32 | 16/32 | N.T. | N.T. | ≤4 | <4 | 3/8 | N.T. |
| MSSA (clinical strain 2) | 32 | 16 | 16 | N.T. | N.T. | ≤4 | 4/8 | ≤2 | N.T. |
| MRSA (clinical strain 1) | 32 | 32 | 32 | N.T. | N.T. | >16 | <4 | <4 | N.T. |
| MRSA (clinical strain 2) | 32 | 32 | 32 | N.T. | N.T. | >16 | 8/16 | >8 | N.T. |

Unit: Concentration (μg/mL)
* In this table, in the case where MICs obtained by testing twice were matched, one value was shown; and, in the case where MICs obtained by testing twice were not matched, values obtained from the first test and the second test were shown respectively.
* N.T.: not tested.

TABLE 8-2

| | Bacterial Name | SR-07 | SR-08 | AP 00196 | Chloramphenicol | Amphotericin B | Tobramycin | Meropenem | Oxacillin | Ciprofloxacin |
|---|---|---|---|---|---|---|---|---|---|---|
| Anaerobic bacteria | *Enterococcus faecalis* | 64 | 32 | 64 | 4 | N.T. | N.T. | N.T. | N.T. | N.T. |
| | *Acinetobacter baumanni* | 8 | 16 | 4/8 | 16/32 | N.T. | N.T. | N.T. | N.T. | N.T. |
| | *Bacteroides fragilis* | 32 | 64/128 | 1 | 1 | N.T. | N.T. | N.T. | N.T. | N.T. |
| | *Clostridium ramosum* | 32 | 32/16 | 32/64 | 4 | N.T. | N.T. | N.T. | N.T. | N.T. |
| | *Fusobacterium nucleatum* | 32/16 | 128 | 2/4 | 0.25 | N.T. | N.T. | N.T. | N.T. | N.T. |
| Fungi | *Penicillium glabrum* (*Penicillium frequentans*) | 16/8 | 8 | 16 | N.T. | 0.125 | N.T. | N.T. | N.T. | N.T. |
| | *Fusarium solani* | 8 | 4/8 | 4/8 | N.T. | 1 | N.T. | N.T. | N.T. | N.T. |
| | *Alternaria alternata* | 32 | 32 | 64 | N.T. | 1 | N.T. | N.T. | N.T. | N.T. |
| | *Trichophyton mentagrophytes* | 32 | 64 | 32 | N.T. | 0.125 | N.T. | N.T. | N.T. | N.T. |
| | *Trichophyton rubrum* | 64 | 128/64 | 64 | N.T. | 0.25 | N.T. | N.T. | N.T. | N.T. |
| | *Candida krusei* | 32 | 16 | 16 | N.T. | 2 | N.T. | N.T. | N.T. | N.T. |

Unit: Concentration (μg/mL)
* In this table, in the case where MICs obtained by testing twice were matched, one value was shown; and, in the case where MICs obtained by testing twice were not matched, values obtained from the first test and the second test were shown respectively.
* N.T.: not tested.

It was proved also from these results that the polypeptides of SR-07 and SR-08 had broad antibacterial spectra.

4. Lumen Formation Test

Then, in order to examine the angiogenesis activity of these, lumen formation by the polypeptides was evaluated using an angiogenesis kit available from KURABO INDUSTRIES LTD. (Product No.: KZ-1000). Vascular endothelial growth factor (VEGF) as a positive control, and polypeptide-free, unstimulated group as a negative control, were used.

Using a special medium for angiogenesis which was attached to the kit, each polypeptide was prepared such that the concentration thereof was respectively 0.5, 2.5 and 10 μg/mL. To a 24-well plate in which cells were plated (the cells were those obtained by co-culturing human vascular endothelial cells and fibroblast cells at an optimum concentration) which was attached to the kit, the special medium for angiogenesis containing each polypeptide was added, and the cells were cultured at 37° C. under 5% $CO_2$. The medium was replaced with a medium containing the same additive on Day 4, Day 7 and Day 9 of culture. On Day 11 from the beginning of the culture, staining was performed using a kit for staining lumina (for CD31 antibody staining) according to the following procedure.

The media were removed, and washing was performed with Dulbecco's phosphate buffered saline (PBS(−)). Thereafter, ice-cooled 70% ethanol was added to the plate, and the cells were fixed. Each well was washed with a blocking solution (Dulbecco's phosphate buffered saline (PBS(−)) containing 1% BSA). To each well, 0.5 mL of the primary antibody for CD31 staining (mouse anti-human CD31 antibody) 4000-fold diluted with the blocking solution was added, and then the plate was incubated for 60 minutes at 37° C. After the completion of the incubation, each well was washed totally 3 times with 1 mL of the blocking solution. Then, 0.5 mL of a secondary antibody solution (goat anti-mouse IgG/alkaline phosphatase conjugate) 500-fold diluted with the blocking solution was added to each well. The plate was incubated for 60 minutes at 37° C., and thereafter each well was washed 3 times with 1 mL of distilled water. During that period, 2 tablets of BCIP/NBT were dissolved into distilled water, and the obtained solution was filtered through a filter having a pore size of 0.2 μm to prepare a substrate solution. To each well, 0.5 mL of the prepared BCIP/NBT substrate solution was added, and the plate was incubated at 37° C. until the lumina turned to deep purple (typically for 5-10 minutes). After the completion of the incubation, each well was washed 3 times with 1 mL of distilled water. After washing, the washing solution was removed by aspiration, and the plate was left to stand and dry naturally. After drying, photographs of each well were taken under a microscope.

Each of the obtained images was quantified using an angiogenesis quantification software. The areas of formed lumina observed in each visual field were measured on the basis of the scale of an angiogenesis quantification software available from KURABO INDUSTRIES LTD. (angiogenesis quantification software Ver 1.0), and evaluated on the basis of the ratio of the areas of polypeptide-containing groups relative to the area of the negative control group.

The results are shown in FIG. 1. In this figure, relative values when taking the negative control as 100 are shown. From these results, it was proved that both SR-07 and SR-08 individually showed an ability to form lumen at the tested concentrations.

5. Collagen Production Test

Normal human dermal fibroblasts (NHDFs) were plated in a 48-well plate. As a medium, Medium 106 containing 1% FBS was used. After culturing in an incubator at 37° C. under 5% $CO_2$ for about 3 hours, the peptide or FGFb (Positive Control), which had been diluted with the medium to each concentration, was added, and the culturing was further continued. The medium was replaced with a medium containing the same additive on Day 3, and the culturing was continued for another 2 days.

The amount of produced collagen was measured by using Semi-Quantitative Collagen Assay Kit.

After the 5-day culture, the medium was removed by aspiration, and the cells were washed with cold PBS(−). Cold methanol/ethanol was added thereto and the plate was left to stand for 10 minutes at room temperature to fix the cells. The cells were washed twice with cold PBS(−). Then, a staining solution (Dye Solution) was added to each well, and the plate was left to stand at room temperature for 30 minutes. The staining solution was removed, and the cells were washed 4-5 times with deionized water. An extraction solution (Dye Extraction Solution) was added to each well to extract the dye, and the absorbances of the extract at 540 nm and 605 nm were measured.

The amounts of collagen and noncollagen proteins were calculated according to the following equation.

Collagen (μg/well)=[OD540−(OD605×0.291)]/37.8×1000

Noncollagen Proteins (μg/well)=OD605/2.04×1000

Figure 2:
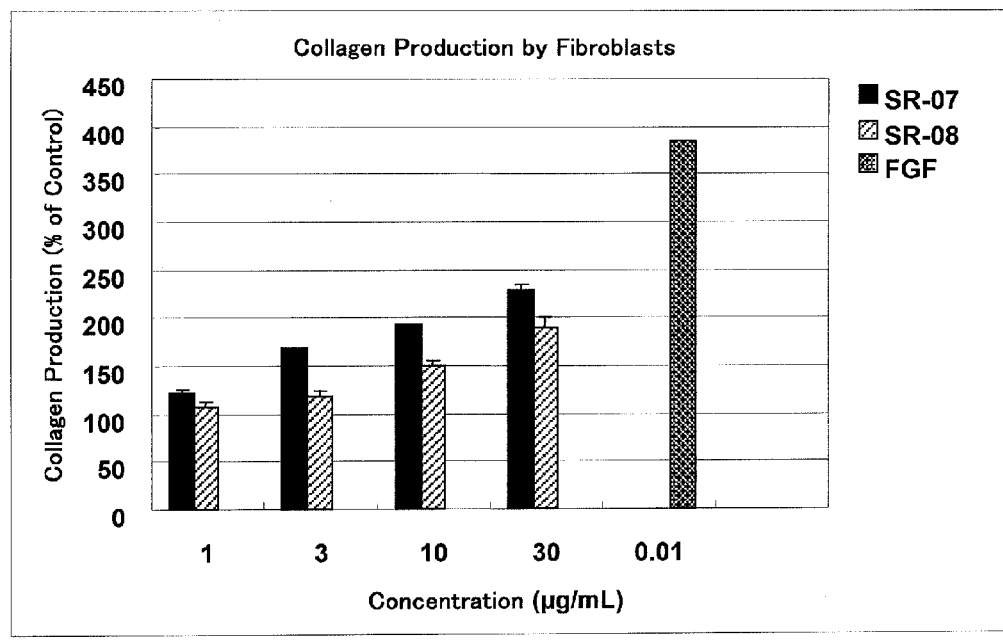
FIG. 2 shows the results of collagen production test performed on the polypeptides SR-07 and SR-08 which are the examples of the present invention.

The results are shown in FIG. 2. As shown in FIG. 2, it was proved that both SR-07 and SR-08 individually had an effect to induce collagen production of the fibroblasts.

6. Effect on Human Umbilical Vein Endothelial Cell Growth

Next, the effect of these polypeptides on the growth of human umbilical vein endothelial cells (HUVECs) was studied. A cell growth activity of the polypeptides was examined using Cell Counting Kit (WST-1) available from Dojindo Laboratories. As a negative control (Control), polypeptide-free group was used. Cells (human umbilical vein endothelial cells: HUVECs) were plated in a 96-well plate ($0.5 \times 10^4$ cells/well/100 μL, serum 1%). About 3 hours after plating the cells, the polypeptides (1, 3, 10, 30 or 100 μg/ml) and FGF (100 ng/ml) as a positive control were individually added thereto in an amount of 100 μL. To the unstimulated group, only a medium was added in an amount of 100 μL. The plate was left to stand in a $CO_2$ incubator for about 48 hours. Thereafter, WST-1 reagent was added to each well in an amount of 20 μL, and then the plate was left to stand in a $CO_2$ incubator for about 2 hours. Absorbances at wavelengths of 450 nm and 620 nm were measured using Wallac 1420 ARVOsx (Program: WST-1). A value of $O.D._{450}-O.D._{620}$ was calculated for each measurement. The values obtained by subtracting the average of values of $O.D._{450}-O.D._{620}$ of blank wells which did not contain cells from values of $O.D._{450}-O.D._{620}$ of the measured wells were regarded as Net $O.D._{450}$. The cell growth activity was evaluated on the basis of the ratio of Net $O.D._{450}$ of polypeptide-containing groups relative to Net $O.D._{450}$ of the unstimulated group.

Figure 3:
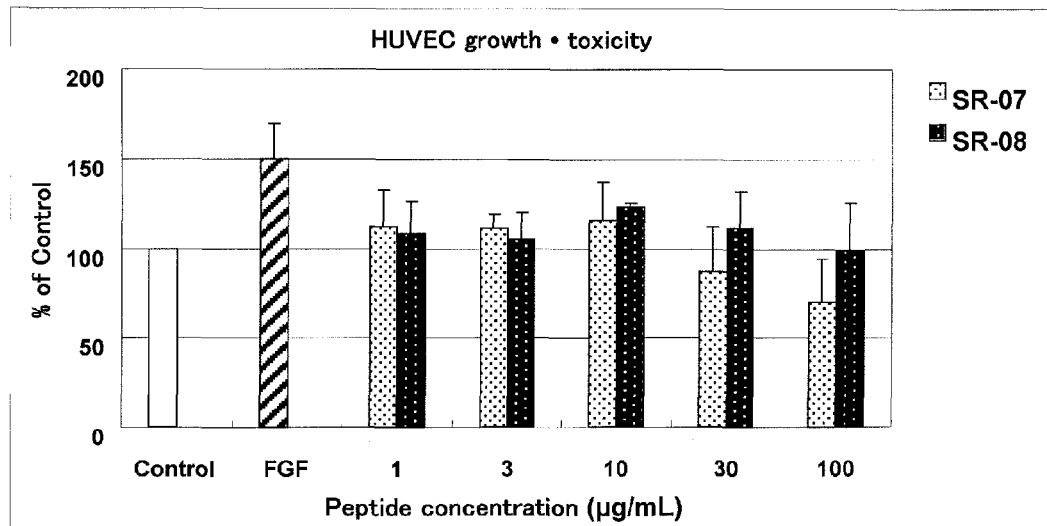
FIG. 3 shows the results obtained by testing the effect of the polypeptides SR-07 and SR-08, which are the examples of the present invention, on the growth of human umbilical vein endothelial cells.

The results are shown in FIG. 3. As shown in FIG. 3, it was proved that SR-07 and SR-08 had an ability to grow HUVECs at a concentration from 1 μg/ml to 10 μg/ml and at a concentration from 1 μg/ml to 30 μg/ml, respectively, and tended to exhibit toxicity at a concentration higher than those.

7. Effect on Normal Human Dermal Fibroblast Growth

Then, the effect on the growth of normal human dermal fibroblasts (NHDFs) was also studied by the same method as described above.

Figure 4:
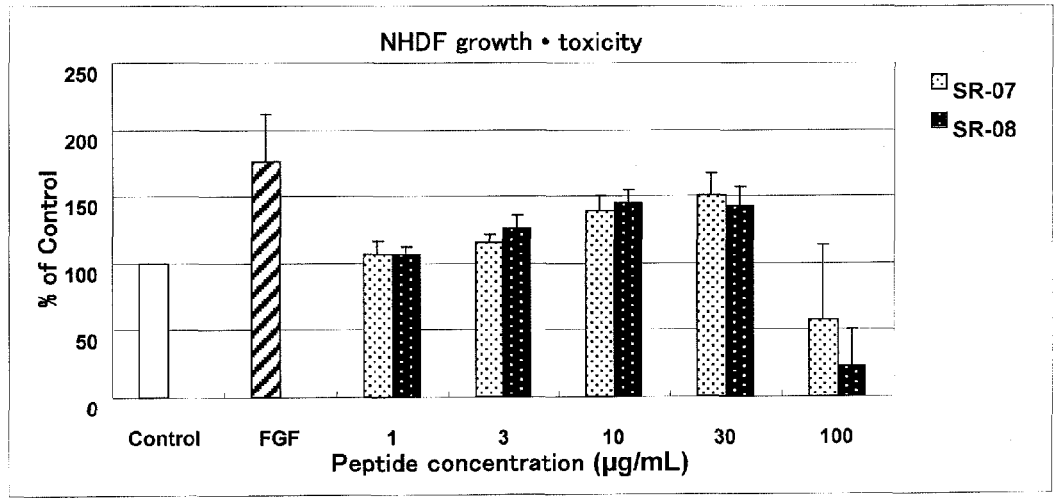
FIG. 4 shows the results obtained by testing the effect of the polypeptides SR-07 and SR-08, which are the examples of the present invention, on the growth of normal human dermal fibroblasts.

The results are shown in FIG. 4. As shown in FIG. 4, it was proved that SR-07 and SR-08 individually had an ability to grow NHDFs at a concentration from 1 μg/ml to 30 μg/ml, and tended to exhibit toxicity at a concentration higher than that.

8. Study of Stability in Serum

The stability of the polypeptides in serum was evaluated. In human serum (purchased from KAC Co., Ltd.), or in rat serum obtained by collecting blood from a rat, then leaving the collected blood to stand at room temperature followed by centrifugation, each of the peptides was dissolved so as to attain a final concentration of 500 μg/mL, and the obtained solutions were left to stand at 37° C. After leaving to stand for 3 min or 10 min, these solutions were subjected to HPLC chromatogram analysis to detect peaks of the decomposition products, and calculate the ratio of the concentration of the peptides which remained in the solutions relative to the starting concentration. In addition, the half-lives of the peptides in serum were also calculated.

HPLC chromatogram analysis conditions were as follows.

Column: CAPCELL PAK C18 MGII (S-3 μm, 4.6×150PE, Shiseido Co., Ltd.)

Guard Column: GUARD CARTRIDGE CAPCELL C18 MG (S-3 μm, 4.0×10PE, Shiseido Co., Ltd.)

Column Temperature: 50° C.

Mobile Phase A: 0.025% trifluoroacetic acid solution

Mobile Phase B: 0.025% trifluoroacetic acid-acetonitrile

Flow Rate: 1.0 mL/min

Detector: an ultraviolet absorptiometer (Measurement Wavelength: 220 nm)

Injection volume: 100 μL

Gradient conditions:

TABLE 9

| Time (min) | Mobile phase A (%) | Mobile phase B (%) |
|---|---|---|
| 0 | 100 | 0 |
| 1 | 100 | 0 |
| 15 | 55 | 45 |
| 20 | 55 | 45 |

TABLE 9-continued

| Time (min) | Mobile phase A (%) | Mobile phase B (%) |
|---|---|---|
| 20.1 | 100 | 0 |
| 25 | 100 | 0 |

The results are shown in Table 10.

TABLE 10

| | 0 | 3 | 10 | Half-life (min) |
|---|---|---|---|---|
| Stability in rat serum | | | | |
| SR-07 | 100 | 51 | 16.5 | 4 |
| SR-08 | 100 | 87 | 86.9 | 60 |
| Stability in human serum | | | | |
| SR-07 | 100 | 98 | 64.3 | 15 |
| SR-08 | 100 | 95 | 65.8 | 16 |

As shown in Table 10, in rat serum, SR-08 showed much higher stability than SR-07; but, in human serum, SR-07 and SR-08 showed approximately the same degree of stability.

9. Comparison of the Ability to Form Granulation Tissue in Paper Disc Model

Then, the ability to form granulation tissue of these polypeptides in vivo was studied. Each of the peptides which were test substances and whose concentration was respectively 25, 250 and 2500 μg/mL, the bFGF formulation whose concentration was respectively 2.5, 25 and 250 μg/mL (positive controls) or saline (negative controls) was added to a paper disc (FILTER PAPER φ8 mm, ADVANTEC) in an amount of 40 μl, such that, in the final state, the dosage of each peptide was 1, 10 or 100 μg/disc. The prepared paper discs were embedded subcutaneously into the back of Crl:CD (SD) rats (male, 9-week old, obtained from Charles River Laboratories Japan, Inc.). Eight days later, the paper discs were taken out, and the granulation tissues around the paper discs were collected to determine their wet weight.

Figure 5:
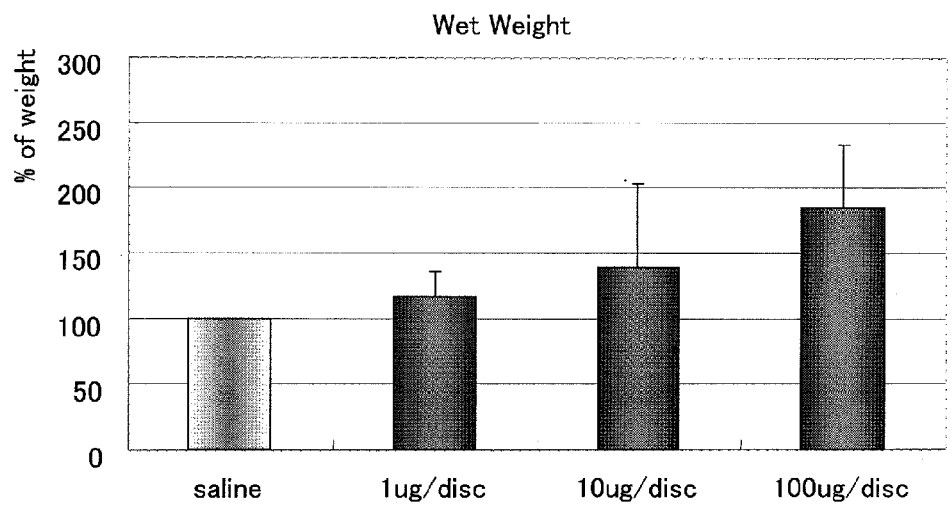
FIG. 5 shows the results obtained by testing the ability to form granulation tissue of the polypeptide SR-07, which is the example of the present invention, in paper disc model.
Figure 6:
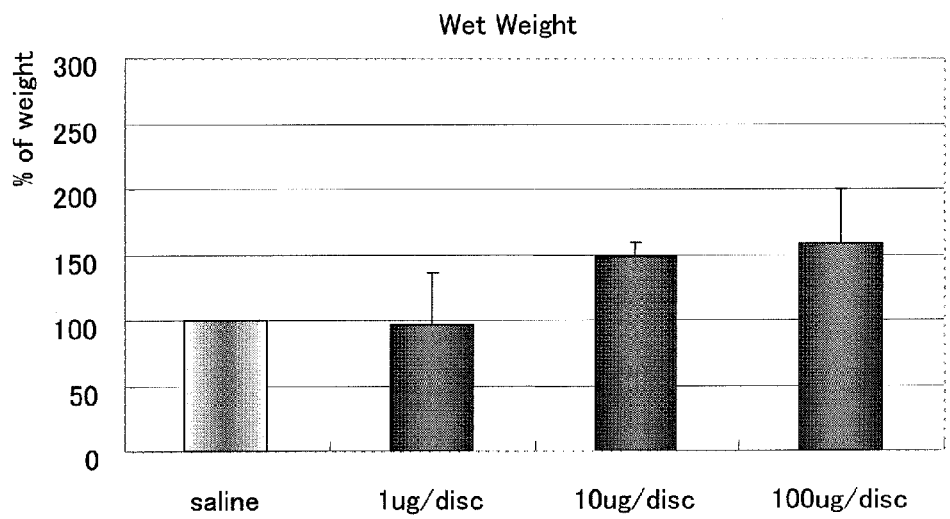
FIG. 6 shows the results obtained by testing the ability to form granulation tissue of the polypeptide SR-08, which is the example of the present invention, in paper disc model.

The results are shown in FIG. 5 (SR-07) and FIG. 6 (SR-08). As shown in FIGS. 5 and 6, it was proved that both SR-07 and SR-08 individually promoted granulation tissue formation in vivo.

10. Effect to Heal Cut Wounds

Next, using rat cut-wound model, the effect of the polypeptides, SR-07 and SR-08, to heal cut wounds in vivo was evaluated. As described in Tetsuaki Yamaura et al. (Oyo Yakuri (Pharmacometrics) 22, 565-579 (1981)), the rat cut-wound model was produced and the wound closing tension was measured.

That is, a cut wound of 30 to 36 mm was made on the back of Crl:CD (SD) rats (male, 7-week old, obtained from Charles River Laboratories Japan, Inc.) using a safety razor, and sutured at 3 points equally spaced. The day when this surgical treatment was applied was regarded as Day 1 (Day 0). Onto the suture site, 50 μL of each of the peptides which were test substances and were respectively prepared to the concentration of 10, 100 and 1000 μg/mL was added dropwise (the added amounts were 500 ng and 5 and 50 μg, respectively). Additions of 50 μL physiological saline were regarded as negative controls (Saline). Each peptide was added dropwise once a day till the day when the measurement of the wound closing tension was carried out. The sutures were removed on Day 3, and the wound closing tension was measured on Day 6.

Figure 7:
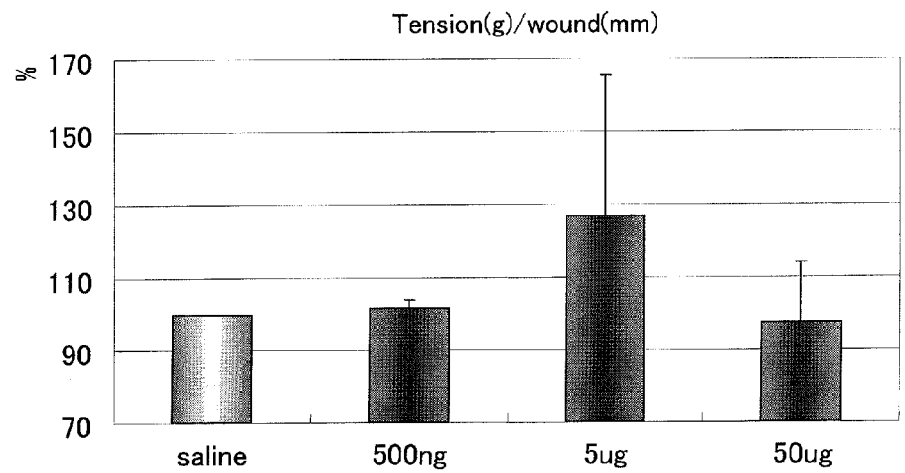
FIG. 7 shows the results obtained by testing the effect to heal a cut wound of the polypeptide SR-07 which is the example of the present invention.
Figure 8:
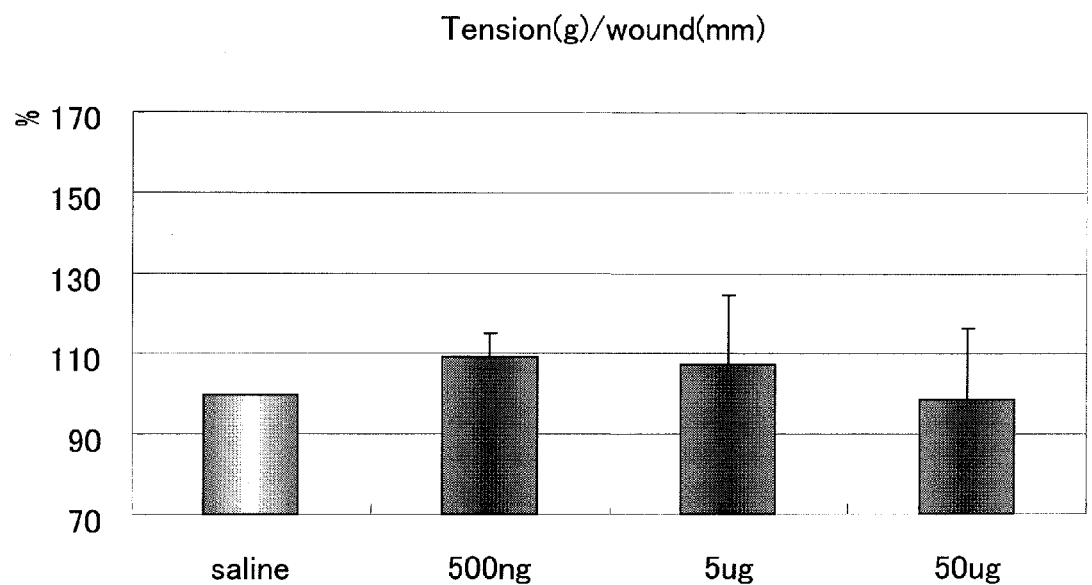
FIG. 8 shows the results obtained by testing the effect to heal a cut wound of the polypeptide SR-08 which is the example of the present invention.

The results are shown in FIG. 7 (SR-07) and FIG. 8 (SR-08). As shown in FIGS. 7 and 8, it was observed that the wound closing tension tended to be increased, suggesting that connective tissue regeneration by fibroblast growth and collagen production and the healing of a cut wound can be promoted.

11. Healing Effect in Infected Wounds

While an effect to promote the healing of a cut wound was proved in the preceding section, in addition to that, a healing effect on a wound infected with *Staphylococcus aureus* was evaluated. Referring to Stenberg B D et al. (J Surg Res. 1991 January; 50(1):47-50.) and Hayward P et al. (Am J Surg. 1992 March; 163(3):288-93.), a rat infected-wound model was produced as described below. HWY/slc hairless rats (male, 7-week old, obtained from Japan SLC, Inc.) were used. The day before full-thickness defects were created, the number of leukocytes was measured and cyclophosphamide was administered in tail vein (100 mg/kg). On the next day, the number of leukocytes was counted. Only the individuals in which the number of leukocytes was not more than 5000, were used. A square-shaped full-thickness defects of 1.73× 1.73 cm (about 3 cm$^2$) were created on the back of the rats, and 25 μL of *Staphylococcus aureus* (about 10$^5$ CFU/25 μL) and SR-07 or SR-08 peptide as a test substance (2 mg/mL) was added dropwise onto the defect sites (the administered amount was 50 μg). On the other hand, 25 μL of the bFGF formulation (3 μg/25 μL) was added dropwise in the bFGF formulation (a positive control) group, and 25 μL of physiological saline was added dropwise in the negative control groups. After administering the test substances, the wound sites were covered with a covering (PERME-ROLL, Nitto Medical Corporation) (Day 0). Thereafter, *Staphylococcus aureus* and the test substance were added dropwise once a day for 4 consecutive days (Days 0, 1, 2 and 3). From the day when the full-thickness defects were created to Day 10, the area where the wounds had still not healed was measured to calculate the ratio of it relative to the area where the wounds were created, and the results were shown in graphs (FIG. 9 (SR-07) and FIG. 10 (SR-08)).

Figure 9:
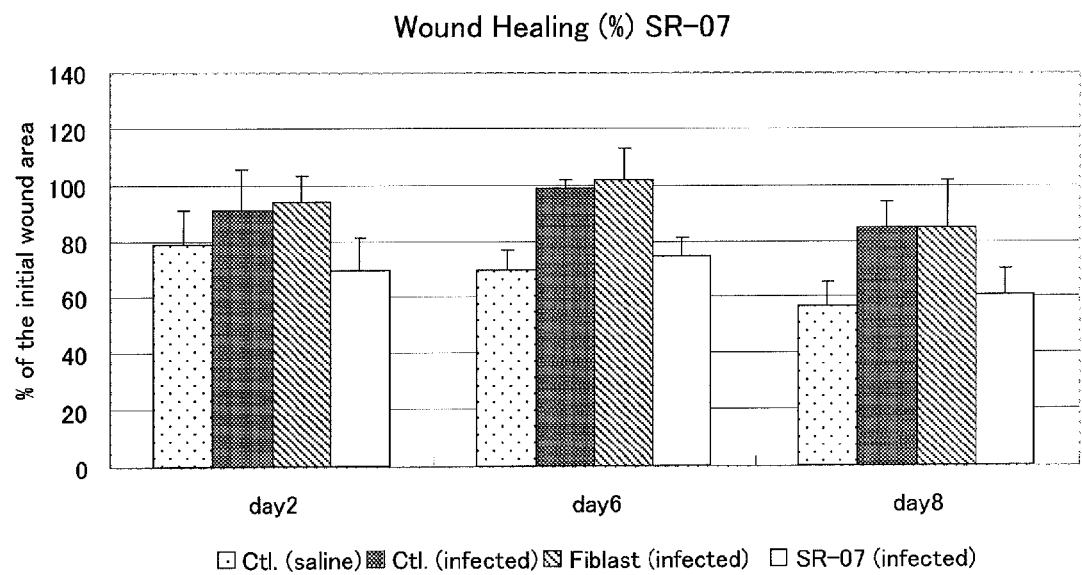
FIG. 9 shows the results obtained by testing the effect to heal an infected wound of the polypeptide SR-07 which is the example of the present invention.
Figure 10:
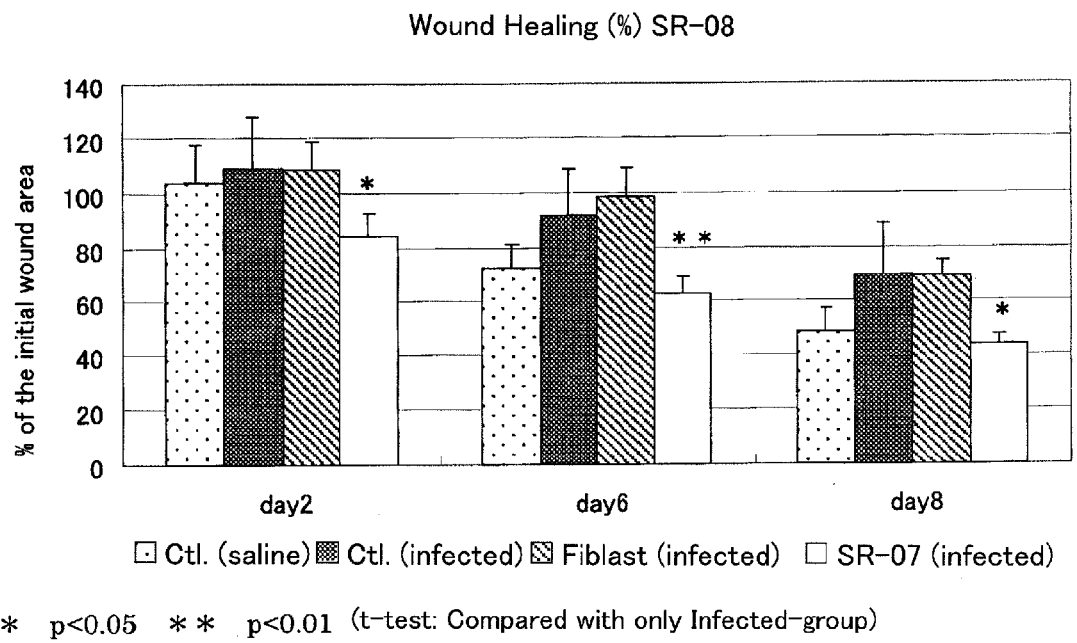
FIG. 10 shows the results obtained by testing the effect to heal an infected wound of the polypeptide SR-08 which is the example of the present invention.

As shown in FIGS. 9 and 10, it was proved that both SR-07 and SR-08 individually showed a higher healing effect on infected wounds than the bFGF formulation (FIBLAST Spray), and these infected wounds were healed at a speed similar to that of the group in which physiological saline had been administered to wounds which had not been associated with infection.

11. Effect to Heal Diabetic Skin Ulcers in Diabetes Flap Model

For the purpose of producing a diabetes model, 7-week old male hairless rats (HWY/slc) were used, and, on the day before full-thickness defect flaps were created, the blood sugar level was measured and streptozotocin was administered once in tail vein (65 mg/kg). The full-thickness defect flap model was produced by measuring the blood sugar level of the rats on the day after the administration of streptozotocin and deciding only the individuals whose blood sugar level was not less than 300 mg/dL as the diabetes model. The full-thickness defect flaps were created by first creating on the back of each rat a pedicle flap of 2×2 cm (square) whose basal part was on its tail side, and then creating a full-thickness defect site (including dermal layer defect) of 1.4×1.4 cm (square: about 2 cm$^2$) in the central part of the created pedicle flap. Then, the flap sites were immediately sutured to obtain the full-thickness defect flap model. The model is a model of a diabetic intractable wound or skin ulcer, since the model also lacks dermal layer. After administering the desired test substance onto the created wound site, the wound site was covered with a covering (PERMEROLL, Nitto Medical Corporation) (Day 0). Thereafter, on every measurement day, the test substance was administered once a day; the change of the area of the wound was calculated by measured values from a digital caliper and digital images; and the area where the wounds had still not healed was measured to calculate the ratio of it relative to the area where the wounds were created (Day 0). The results are shown in FIG. 11.

Figure 11:
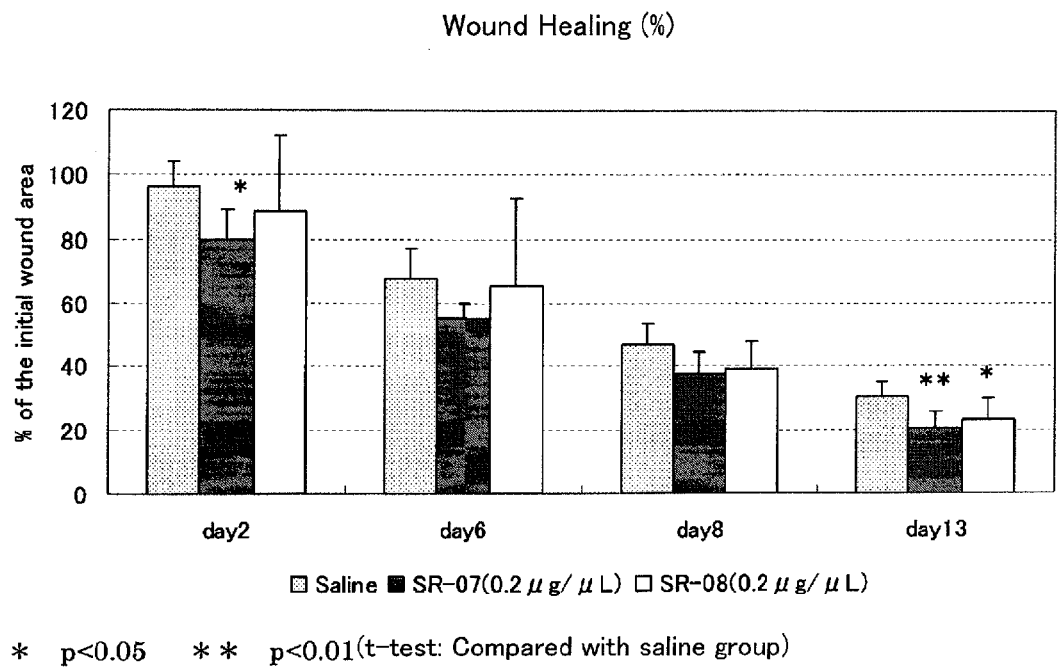
FIG. 11 shows the results obtained by testing the effect to heal an intractable wound of the polypeptides SR-07 and SR-08, which are the examples of the present invention, in diabetes flap model.

As shown in FIG. 11, it was proved that, from immediately after the wound was created, both polypeptides individuality decreased the remaining wound area, compared to the control group in which physiological saline had been administered (Saline), and that the polypeptides of the present invention promote the healing of an intractable wound associated with diabetes.

Figure 12:
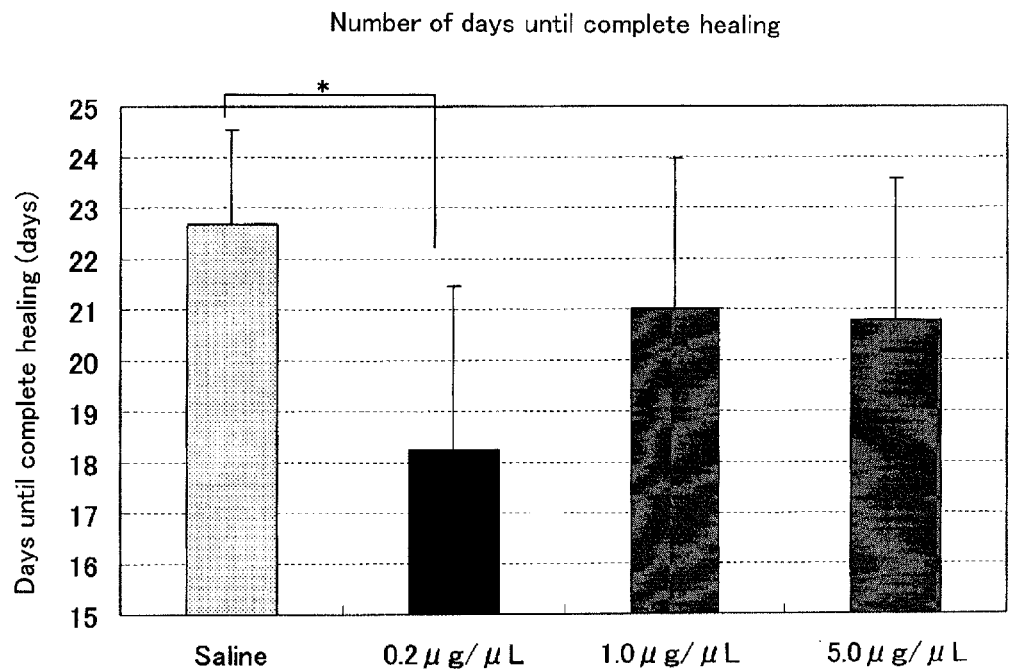
FIG. 12 shows the results obtained by testing the number of days until complete healing of a wound in case of the polypeptide SR-07 which is the example of the present invention.
Figure 13:
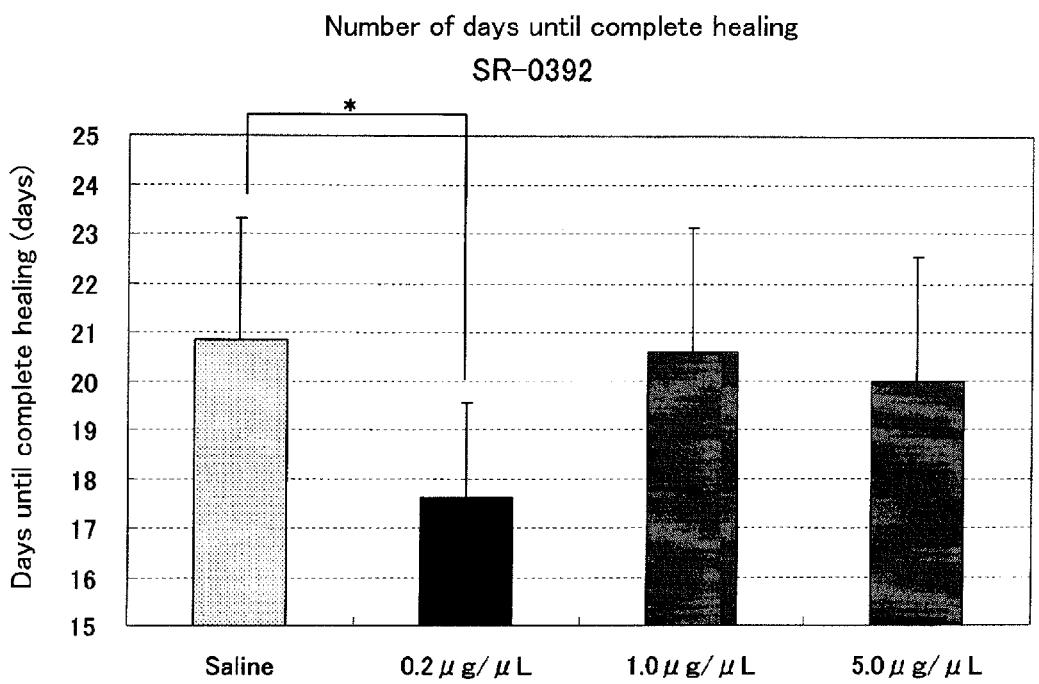
FIG. 13 shows the results obtained by testing the number of days until complete healing of a wound in case of the polypeptide SR-08 which is the example of the present invention.

The numbers of days until complete healing in cases of SR-07 and SR-08 were shown in FIG. 12 (SR-07) and FIG. 13 (SR-08), respectively. The numbers of days until complete healing in the groups in which SR-07 and SR-08 were individually used in an amount of 0.2 µg/µL were significantly smaller than the solvent control group. The same tendency as observed in the evaluation of wound healing rate was also observed in the number of days until complete healing. From these results, it was proved that SR-07 and SR-08, which are the polypeptides of the present invention, individually show a therapeutic effect on skin ulcers and also on diabetic skin ulcers.

12. Effect to Heal Burn Ulcers

A burn model was produced using 7-week old male hairless rats (HWY/slc), and the healing effect of the polypeptides of the present invention was examined. The burn-ulcer model was produced by contacting a red hot iron (at 100° C., φ12 mm) to the back of each rat for 5 seconds under anesthesia with ether to induce a burn. The model had a severe burn in which dermal tissue and muscular tissue also led to necrosis, and it was confirmed that a burn skin ulcer was caused. On the day after inducing the burn, the necrotic skin was surgically removed to obtain a burn model. After producing the burn model, the test substance was administered onto the wound site, and a covering was used to cover over that (Day 0). Only a covering was used in the Control. Thereafter, the test substance was administered once a day on every measurement day. And, on Day 6 and Day 8, the change of the area of the wound was measured by calculating measured values from a digital caliper and digital images, and the area where the burns had still not healed was measured to calculate the ratio of it relative to the area where the burns were created (Day 0). The concentration of the test substances were individually 0.2 µg/µL (20 µg/wound).

Figure 14:
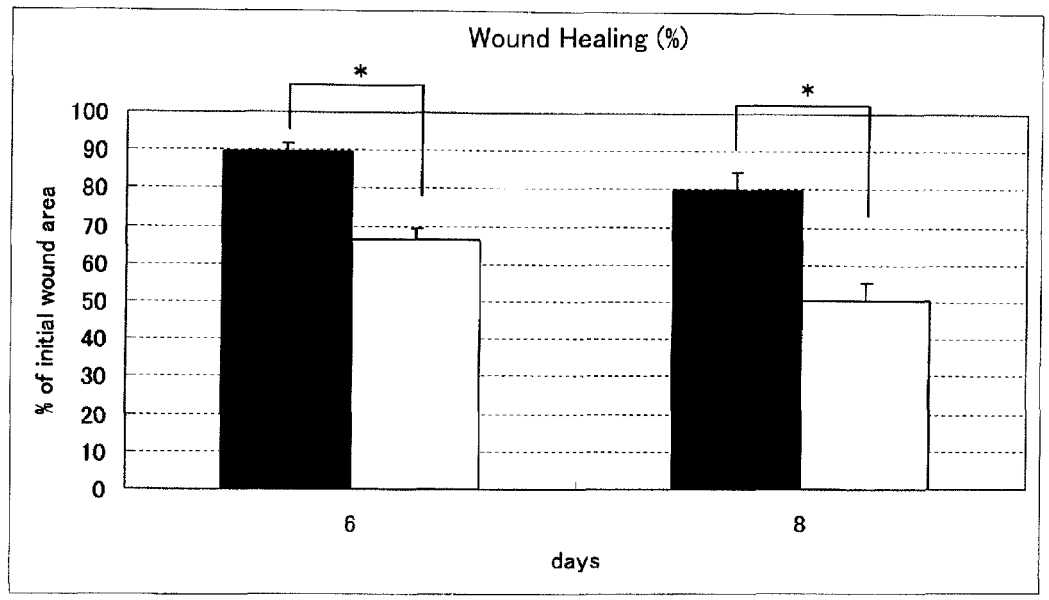
FIG. 14 shows the results obtained by testing the effect to heal a burn of the polypeptide SR-07 which is the example of the present invention.
Figure 15:
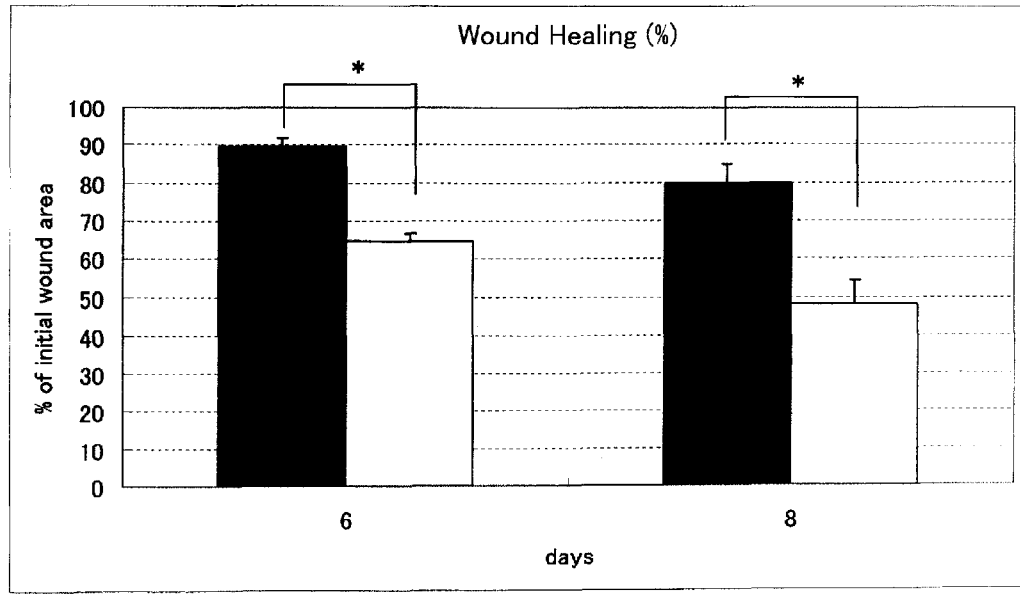
FIG. 15 shows the results obtained by testing the effect to heal a burn of the polypeptide SR-08 which is the example of the present invention.

The results are shown in FIG. 14 (SR-07) and FIG. 15 (SR-08). In both the graphs, the black bars show Controls and the white bars show the peptides. As shown in FIGS. 14 and 15, it was proved that SR-07 and SR-08, which are the polypeptides of the present invention, individually showed a therapeutic effect also in the burn-ulcer model.

13. Healing Effect on Decubituses

In order to confirm the healing effect on a decubitus, one of skin ulcers, a decubitus model was produced using 7-week old male hairless rats (HWY/slc), and the healing effect of the polypeptides of the present invention was examined. A pair of magnets (φ10×5 mm; available from AZBIO KENIS; rare earth magnets; Type: KD-2; Code: 3-118-119; and, Magnetic Flux Density: 350 mT) was contacted to the skin of the back of each rat for 8 hours to induce a decubitus. On the day after inducing the decubitus, the necrotic skin was surgically removed to obtain a decubitus model. After producing the decubitus model, the test substance was administered onto the wound site, and a covering was used to cover over that (Day 0). Only a covering was used in the Control. Thereafter, on every measurement day, the test substance was administered once a day, and the change of the area of the wound was measured by calculating measured values from a digital caliper and digital images. The concentration of the test substances were individually 0.2 µg/uL (4 µg/wound). The area where the burns had still not healed was measured to calculate the ratio of it relative to the area where the burns were created (Day 0).

Figure 16:
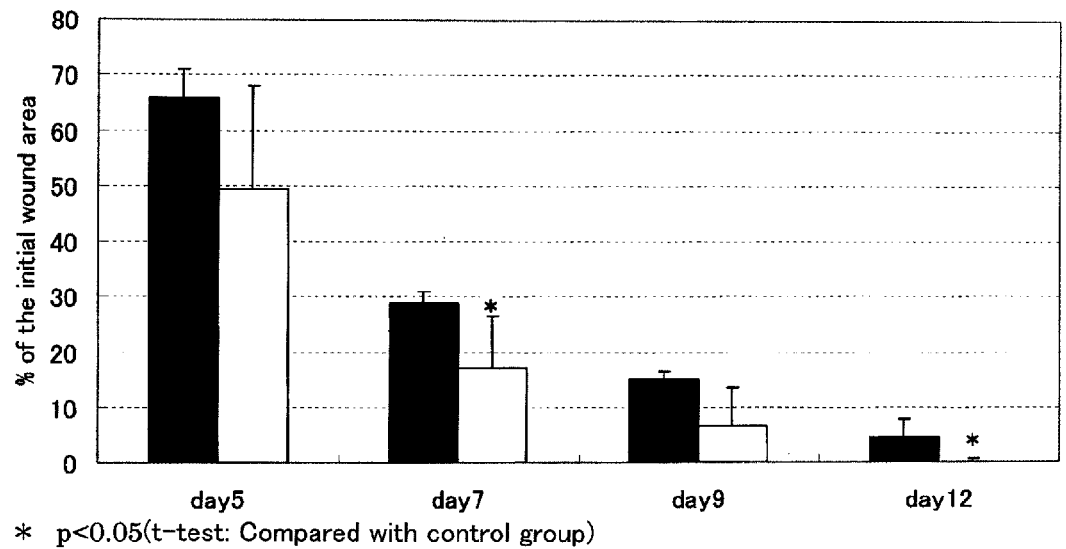
FIG. 16 shows the results obtained by testing the healing effect on a decubital ulcer of the polypeptide SR-07 which is the example of the present invention.
Figure 17:
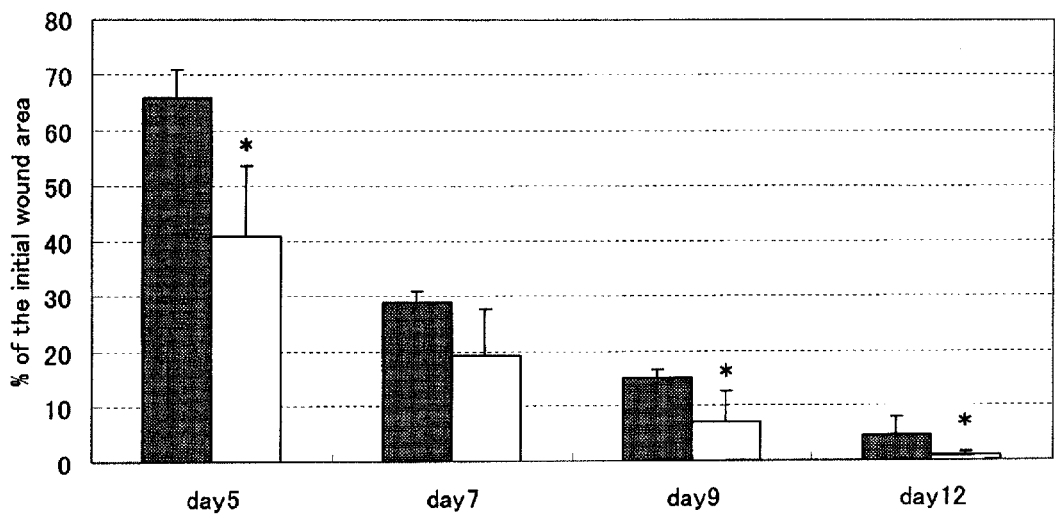
FIG. 17 shows the results obtained by testing the healing effect on a decubital ulcer of the polypeptide SR-08 which is the example of the present invention.

The results are shown in FIG. 16 (SR-07) and FIG. 17 (SR-08). In both the graphs, the black bars show Controls and the white bars show the peptides. As shown in FIGS. 16 and 17, it was proved that SR-07 and SR-08, which are the polypeptides of the present invention, individually showed a therapeutic effect also in decubituses.

Furthermore, with respect to these peptides, the results obtained by measuring the ratio of remaining wound area on Day 12 are shown in Tables 11 and 12 below.

TABLE 11

| | SR-07 | |
|---|---|---|
| | | Day 12 |
| Mean Value | Control Group | 4.516729 |
| | SR-07 | 0.149564 |
| SD | Control Group | 3.224151 |
| | SR-07 | 0.334435 |
| p value | SR-07 | 0.01826 |

TABLE 12

| | SR-08 | |
|---|---|---|
| | | Day 12 |
| Mean Value | Control Group | 4.516729 |
| | SR-08 | 0.790159 |
| SD | Control Group | 3.224151 |
| | SR-08 | 0.847383 |
| p value | SR-08 | 0.039897 |

As shown in Tables 11 and 12, on Day 12, it is found that the healing was significantly promoted in the groups in which SR-07 and SR-08, which are the polypeptides of the present invention, had been administered.

14. Evaluation of Skin Tissue in Cut Wound Healing

A cut-wound model was produced using 7-week old male SD rats (Crl:CD), and the change in the skin tissue caused by administering the polypeptides of the present invention was evaluated. A cut wound of 30 to 36 mm was made on the back of the rats using a safety razor, and sutured at 3 points equally spaced (Day 0). Onto the suture site, 50 µL of each of the test substances which were respectively adjusted to the concentration of 200 µg/mL was added dropwise (the added amount was 10 µg). Each test substance was administered dropwise once a day till the day when the sutures were removed. On Day 3 after the suturing, the sutures were removed; and, on Day 6, the skin tissue in the cut wound site was collected to evaluate the skin by HE staining As a result of observation, thickening in stratum spinosum epidermidis (indicated by the arrow in the upper right figure) was observed in Saline group. Further, a number of neutrophils and fibroblasts were observed around the cut wound site. In cases of SR-07 and SR-08, the thickening in stratum spinosum epidermidis was less than the saline group, and a phenomenon that the fibroblasts were replaced to collagen sooner than the sailine group was observed. In cases of SR-07 and SR-08, not only was it observed that the granulation and collagen was increased compared to Saline, but also it was proved that the wound healing was promoted while suppressing the thickening.

What is claimed is:

1. A method for the amelioration or treatment of a condition in a mammal, wherein said condition is selected from the group consisting of: burns, wounds, erosions, skin ulcers and intractable wounds, said method comprising administering to said mammal an effective amount of a polypeptide consisting of the amino acid sequence of SEQ ID NO:8 or SEQ ID NO:10.

2. The method of claim 1, wherein said polypeptide is part of a pharmaceutical composition which further comprises a pharmaceutically acceptable carrier.

3. The method of claim 2, wherein said polypeptide is present in said pharmaceutical composition at a concentration of 0.001 mg/mL to 10 mg/mL.

4. The method of claim 2, wherein said polypeptide is present in said pharmaceutical composition at a concentration of 0.1 mg/mL to 5 mg/mL.

5. The method of claim 1, wherein the condition is selected from the group consisting of: burns, wounds, erosions, skin ulcers and intractable wounds associated with bacterial or fungal infection.

6. The method of claim 1, wherein said polypeptide is administered topically.

7. The method of claim 6, wherein the condition is selected from the group consisting of: burns, wounds, erosions, skin ulcers and intractable wounds associated with bacterial or fungal infection.

8. The method of claim 1, wherein said polypeptide is administered to a human to ameliorate or treat said condition, and said polypeptide consists of the amino acid sequence of SEQ ID NO:8.

9. The method of claim 8, wherein said polypeptide is part of a pharmaceutical composition which further comprises a pharmaceutically acceptable carrier.

10. The method of claim 9, wherein said polypeptide is present in said pharmaceutical composition at a concentration of 0.001 mg/mL to 10 mg/mL and is administered topically.

11. The method of claim 9, wherein said polypeptide is present in said pharmaceutical composition at a concentration of 0.1 mg/mL to 5 mg/mL and is administered topically.

12. The method of claim 1, wherein said polypeptide is administered to a human to ameliorate or treat said condition, and said polypeptide consists of the amino acid sequence of SEQ ID NO:10.

13. The method of claim 12, wherein said polypeptide is part of a pharmaceutical composition which further comprises a pharmaceutically acceptable carrier.

14. The method of claim 13, wherein said polypeptide is present in said pharmaceutical composition at a concentration of 0.001 mg/mL to 10 mg/mL and is administered topically.

15. The method of claim 13, wherein said polypeptide is present in said pharmaceutical composition at a concentration of 0.1 mg/mL to 5 mg/mL and is administered topically.

* * * * *